United States Patent
Fischetti et al.

(10) Patent No.: US 11,015,182 B2
(45) Date of Patent: *May 25, 2021

(54) CHIMERIC BACTERIOPHAGE LYSIN WITH ACTIVITY AGAINST STAPHYLOCOCCI BACTERIA

(71) Applicant: THE ROCKEFELLER UNIVERSITY, New York, NY (US)

(72) Inventors: Vincent A. Fischetti, New York, NY (US); Anu Daniel, New York, NY (US); Chad Euler, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/105,155

(22) Filed: Aug. 20, 2018

(65) Prior Publication Data
US 2019/0055533 A1   Feb. 21, 2019

Related U.S. Application Data

(63) Continuation of application No. 14/480,822, filed on Sep. 9, 2014, now Pat. No. 10,053,681, which is a continuation of application No. 13/502,912, filed as application No. PCT/US2009/049349 on Jul. 1, 2009, now Pat. No. 8,840,900.

(60) Provisional application No. 61/078,277, filed on Jul. 3, 2008.

(51) Int. Cl.
*C12N 9/36*  (2006.01)
*A01N 63/00*  (2020.01)
*C07K 14/005*  (2006.01)
*A61K 38/00*  (2006.01)
*A61K 38/47*  (2006.01)

(52) U.S. Cl.
CPC .......... *C12N 9/2462* (2013.01); *A01N 63/00* (2013.01); *C07K 14/005* (2013.01); *A61K 38/00* (2013.01); *A61K 38/47* (2013.01); *C07K 2319/00* (2013.01); *C12N 2795/10322* (2013.01)

(58) Field of Classification Search
None
See application file for complete search history.

(56) References Cited

U.S. PATENT DOCUMENTS

2004/0105852 A1   6/2004  Pischetti et al.
2004/0213765 A1   10/2004 Fischetti et al.

FOREIGN PATENT DOCUMENTS

WO   WO 02/094868 A2 * 11/2002
WO   WO09024327      2/2009

OTHER PUBLICATIONS

GenBank accession No. CAA69021 May 26, 1999.*
Of NCBI Reference sequence YP_908849.1 Dec. 5, 2006.*
GenBank Accession # AAX91129, Apr. 15, 2005.*
Uniprot Accession # A7TWR7 Oct. 2, 2007.*
Uniprot Accession # A0EX11 Nov. 28, 2006.*
GenBank Accession ABS87584.1 Amidadse *Staphylococcus* phage tp310-3 Aug. 30, 2007.*
Diaz, E et al (1990) Chimeric phage-bacterial enzymes: a clue to the modular evolution of genes Proc Natl Acad Sci 87(20):8125-8129.
Kwan, T et al (2005) The complete genomes and proteomes of 27 *Staphylococcus aureus* bacteriophages Proc Natl Acad Sci 102(14):5174-5179.
Loessner, MJ et al (1998) The two-component lysis system of *Staphylococcus aureus* bacteriophage Twort: a large TTG-start holin and an associated amidase endolysin FEMS Microbiol Lett 162(2):265-274.
Manoharadas, S et al (2009) Antimicrobial activity of a chimeric enzybiotic towards *Staphylococcus aureus* J Biotechnol 139(1):118-123.
O'Flaherty, S et al (2005) The recombinant phage lysin LysK has a broad spectrum of lytic activity against clinically relevant staphylococci, including methicillin-resistant *Staphylococcus aureus* J Bacteriol 187(20):7161-7164.
Uniprot Q4ZE009 (Q4ZE09_9CAUD) Unreviewed, UniProtKB/TrEMGL Oct. 19, 2011, Version 18.
Ahmed, ABF et al (2007) Evaluation of cell wall binding domain of *Staphylococcus aureus* autolysin as affinity reagent for bacteria and its application to bacterial detection J Biosci & Bioeng 104(1):55-61.
Aksoy, DY et al (2008) New antimicrobial agents for the treatment of Gram-positive bacterial infections Clin Microbiol Infect 14(5):411-420.
Cheng, Q et al (2005) Removal of group B streptococci colonizing the vagina and oropharynx of mice with a bacteriophage lytic enzyme Antimicrob Agents Chemother 49(1):111-117.
Croux, C et al (1993) Interchange of functional domains switches enzyme specificity: construction of a chimeric pneumococcal-clostridial cell wall lytic enzyme Mol Microbiol 9(5):1019-1025.
Donovan, DM et al (2006) Peptidoglycan hydrolase fusions maintain their parental specificities Appl Environ Microbiol 72(4):2988-2996.
Fischetti, VA (2005) Bacteriophage lytic enzymes: novel anti-infectives Trends in Microbiol 13(10):491-496.
Fischetti, VA et al (2006) Reinventing phage therapy: are the parts greater than the sum? Nat Biotechnol 24(12):1508-1511.
Loeffler, JM et al (2001) Rapid killing of *Streptococcus pneumoniae* with a bacteriophage cell wall hydrolase Science 29(5549):2170-2172.
Loessner, MJ (2005) Bacteriophage endolysins—current state of research and applications Curr Opin in Micro 8(4):480-487.

(Continued)

*Primary Examiner* — Oluwatosin A Ogunbiyi
(74) *Attorney, Agent, or Firm* — Hoffmann & Baron LLP

(57) ABSTRACT

The present disclosure relates to chimeric bacteriophage lysins useful for the identification and/or reduction of staphylococcal populations. For example, a chimeric bacteriophage lysin was engineered and shown to effectively kill all strains of staphylococci tested including antibiotic resistant methicillin-resistant *S. aureus* (MRSA) and vancomycin intermediate *S. aureus* (VISA).

25 Claims, 18 Drawing Sheets

Specification includes a Sequence Listing.

(56) References Cited

OTHER PUBLICATIONS

López, R et al (1997) The pneumococcal cell wall degrading enzymes: a modular design to create new lysins? Microb Drug Res 3(2):199-211.
Lu, JZ et al (2006) Cell wall-targeting domain of glycylglycine endopeptidase distinguishes among peptidoglycan cross-bridges J Biol Chem 281(1):549-558.
Mangili, A et al (2005) Daptomycin-resistant, methicillin-resistant Staphylococcus aureus bacteremia Clin Infect Dis 40(7):1058-1060.
Nelson, D et al (2001) Prevention and elimination of upper respiratory colonization of mice by group A streptococci by using a bacteriophage lytic enzyme Proc Natl Acad Sci USA 98(7):4107-4112.
Nelson, D et al (2006) PlyC: a multimeric bacteriophage lysin Proc Natl Acad Sci 103(28):10765-10770.
Rashel, M et al (2007) Efficient elimination of multidrug-resistant Staphylococcus aureus by cloned lysin derived from bacteriophage phi MR11 J Infect Dis 196(8):1237-1247.
Schuch, R et al (2002) A bacteriolytic agent that detects and kills Bacillus anthracis Nature 418(6900):884-889.
Sheehan, MM et al (1996) Analysis of the catalytic domain of the lysin of the lactococcal bacteriophage Tuc 2009 by ahimeric gene assembling FEMS Microbiol Lett 140(1):23-28.
Skiest, DJ (2006) Treatment failure resulting from resistance of Staphylococcus aureus to daptomycin J. Clin Microbiol 44(2):655-656.
Tsiodras, S et al (2001) Linezolid resistance in a clinical isolate of Staphylococcus aureus Lancet 358(9277):207-208.
Yoong, P. et al (2004) Identification of a broadly active phage lytic enzyme with lethal activity against antibiotic-resistant Enterococcus faecalis and Enterococcus faecium J Bacterid 186(14):4808-4812.
Bae, T., et al (2006) "Prophages of Staphylococcus aureus Newman and their contribution to virulence". Molecular Microbiology, 62(4): 1035-1047, doi:10.1111/j.1365-2958.2006.05441.x.

\* cited by examiner

Figure 2B

GKSASKITVGSKAPYNLKWSKGAYFNAKIDGLGATSATRYGDNRTNYRFDVGQAVYAPGTLIYVFEIIDGWCRIYWNNHNEWIWHERLIVKEVF

SEQ ID NO:1

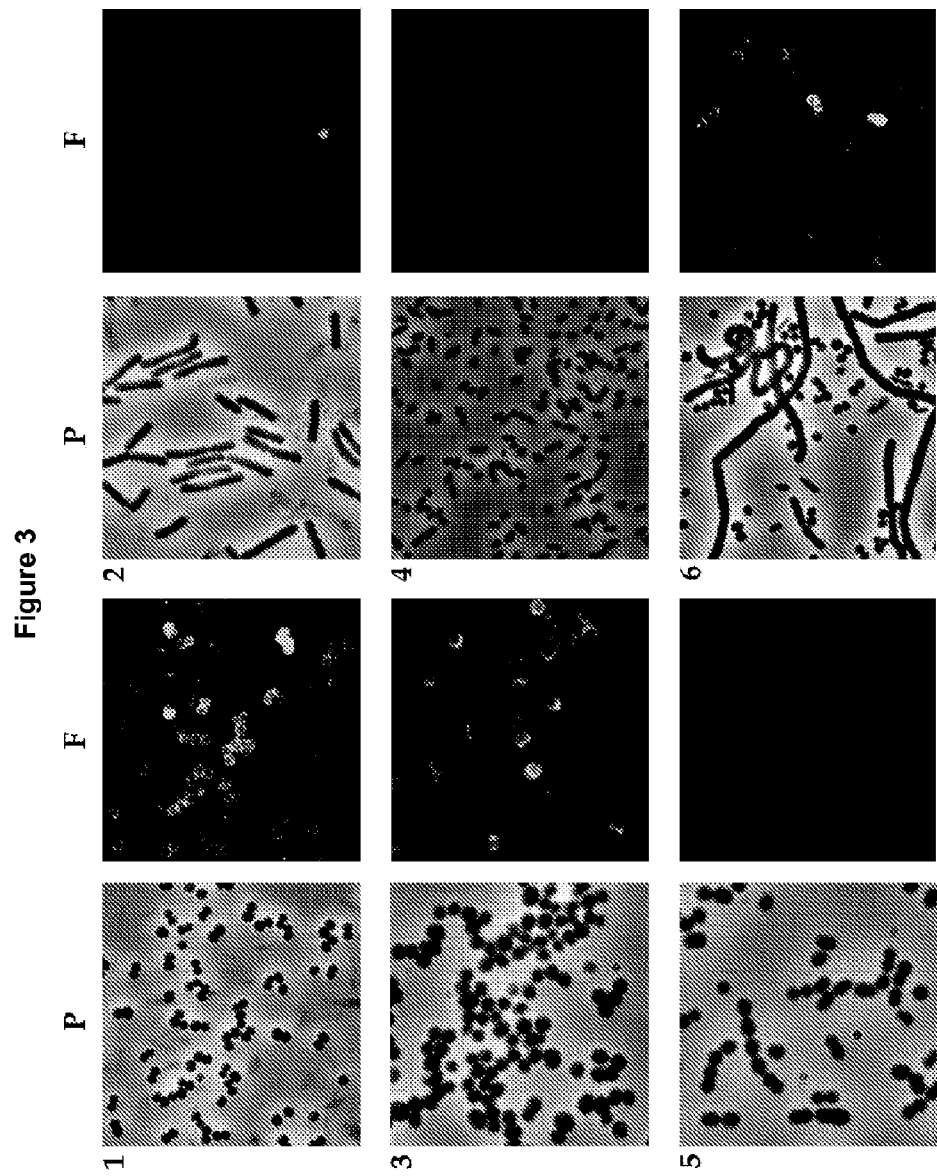

SEQ ID NO:2 ClyS (AD127)

Figure 5B

METLKQAESYIKSKVNTGTDFDGLYGYQCMDLLAVDYIYHVTDGKIRMWGNAKDAINNSFGGTATVYRNYPAFRPKYGDVVWTTGNFATYGHIAIVTNPDPYGDLQYVTVLEQNWNGNGI

YKTELATIRTHFDYTGITHFIRPNFATESSVKKDTKKKPKPSNRDGINKDKIVYDRTNINYNMVLQTPNTGWKTNKYGTLYKSESASFTPNTDIITRTTGPRSMPQSGVLKAGQTIHYD

EVMKQDGHVWVGYTGNSGQRIYLPVRTWNKSTNTLGVLWGTIK.

SEQ ID NO:3 (AD119)

Viability and lytic assay

SEQUENCE LISTING

<160> NUMBER OF SEQ ID NOS: 17

<210> SEQ ID NO 1
<211> LENGTH: 94
<212> TYPE: PRT
<213> ORGANISM: Staphylococcus aureus phage phiNM3

<400> SEQUENCE: 1

Gly Lys Ser Ala Ser Lys Ile Thr Val Gly Ser Lys Ala Pro Tyr Asn
1               5                   10                  15

Leu Lys Trp Ser Lys Gly Ala Tyr Phe Asn Ala Lys Ile Asp Gly Leu
            20                  25                  30

Gly Ala Thr Ser Ala Thr Arg Tyr Gly Asp Asn Arg Thr Asn Tyr Arg
        35                  40                  45

Phe Asp Val Gly Gln Ala Val Tyr Ala Pro Gly Thr Leu Ile Tyr Val
    50                  55                  60

Phe Glu Ile Ile Asp Gly Trp Cys Arg Ile Tyr Trp Asn Asn His Asn
65                  70                  75                  80

Glu Trp Ile Trp His Glu Arg Leu Ile Val Lys Glu Val Phe
                85                  90

<210> SEQ ID NO 2
<211> LENGTH: 280
<212> TYPE: PRT
<213> ORGANISM: Artificial Sequence

```
<220> FEATURE:
<223> OTHER INFORMATION: Chimeric of Staphylococcus aureus bacteriophage
      Twort domain and Staphylococcus aureus phage phiNM3 CWT domain

<400> SEQUENCE: 2

Met Glu Thr Leu Lys Gln Ala Glu Ser Tyr Ile Lys Ser Lys Val Asn
1               5                   10                  15

Thr Gly Thr Asp Phe Asp Gly Leu Tyr Gly Tyr Gln Cys Met Asp Leu
            20                  25                  30

Ala Val Asp Tyr Ile Tyr His Val Thr Asp Gly Lys Ile Arg Met Trp
        35                  40                  45

Gly Asn Ala Lys Asp Ala Ile Asn Asn Ser Phe Gly Gly Thr Ala Thr
50                  55                  60

Val Tyr Lys Asn Tyr Pro Ala Phe Arg Pro Lys Tyr Gly Asp Val Val
65                  70                  75                  80

Val Trp Thr Thr Gly Asn Phe Ala Thr Tyr Gly His Ile Ala Ile Val
                85                  90                  95

Thr Asn Pro Asp Pro Tyr Gly Asp Leu Gln Tyr Val Thr Val Leu Glu
            100                 105                 110

Gln Asn Trp Asn Gly Asn Gly Ile Tyr Lys Thr Glu Leu Ala Thr Ile
        115                 120                 125

Arg Thr His Asp Tyr Thr Gly Ile Thr His Phe Ile Arg Pro Asn Phe
130                 135                 140

Ala Thr Glu Ser Ser Val Lys Lys Lys Asp Thr Lys Lys Lys Pro Lys
145                 150                 155                 160

Pro Ser Asn Arg Asp Gly Leu Asn Lys Asp Lys Ile Val Tyr Asp Arg
                165                 170                 175

Thr Asn Ile Asn Tyr Asn Met Val Leu Gln Gly Lys Ser Ala Ser Lys
            180                 185                 190

Ile Thr Val Gly Ser Lys Ala Pro Tyr Asn Leu Lys Trp Ser Lys Gly
        195                 200                 205

Ala Tyr Phe Asn Ala Lys Ile Asp Gly Leu Gly Ala Thr Ser Ala Thr
210                 215                 220

Arg Tyr Gly Asp Asn Arg Thr Asn Tyr Arg Phe Asp Val Gly Gln Ala
225                 230                 235                 240

Val Tyr Ala Pro Gly Thr Leu Ile Tyr Val Phe Glu Ile Ile Asp Gly
                245                 250                 255

Trp Cys Arg Ile Tyr Trp Asn Asn His Asn Glu Trp Ile Trp His Glu
            260                 265                 270

Arg Leu Ile Val Lys Glu Val Phe
        275                 280

<210> SEQ ID NO 3
<211> LENGTH: 283
<212> TYPE: PRT
<213> ORGANISM: Artificial Sequence
<220> FEATURE:
<223> OTHER INFORMATION: Chimeric of Staphylococcus aureus bacteriophage
      Twort domain and Staphylococcus simulans metalloendopeptidase
      Lysostaphin CWT domain

<400> SEQUENCE: 3

Met Glu Thr Leu Lys Gln Ala Glu Ser Tyr Ile Lys Ser Lys Val Asn
1               5                   10                  15

Thr Gly Thr Asp Phe Asp Gly Leu Tyr Gly Tyr Gln Cys Met Asp Leu
            20                  25                  30

Ala Val Asp Tyr Ile Tyr His Val Thr Asp Gly Lys Ile Arg Met Trp
```

35                  40                  45
Gly Asn Ala Lys Asp Ala Ile Asn Asn Ser Phe Gly Gly Thr Ala Thr
 50                  55                  60

Val Tyr Lys Asn Tyr Pro Ala Phe Arg Pro Lys Tyr Gly Asp Val Val
 65                  70                  75                  80

Val Trp Thr Thr Gly Asn Phe Ala Thr Tyr Gly His Ile Ala Ile Val
                     85                  90                  95

Thr Asn Pro Asp Pro Tyr Gly Asp Leu Gln Tyr Val Thr Val Leu Glu
                    100                 105                 110

Gln Asn Trp Asn Gly Asn Gly Ile Tyr Lys Thr Glu Leu Ala Thr Ile
                    115                 120                 125

Arg Thr His Asp Tyr Thr Gly Ile Thr His Phe Ile Arg Pro Asn Phe
                    130                 135                 140

Ala Thr Glu Ser Ser Val Lys Lys Lys Asp Thr Lys Lys Lys Pro Lys
145                 150                 155                 160

Pro Ser Asn Arg Asp Gly Leu Asn Lys Asp Lys Ile Val Tyr Asp Arg
                    165                 170                 175

Thr Asn Ile Asn Tyr Asn Met Val Leu Gln Thr Pro Asn Thr Gly Trp
                    180                 185                 190

Lys Thr Asn Lys Tyr Gly Thr Leu Tyr Lys Ser Glu Ser Ala Ser Phe
                    195                 200                 205

Thr Pro Asn Thr Asp Ile Ile Thr Arg Thr Thr Gly Pro Phe Arg Ser
                    210                 215                 220

Met Pro Gln Ser Gly Val Leu Lys Ala Gly Gln Thr Ile His Tyr Asp
225                 230                 235                 240

Glu Val Met Lys Gln Asp Gly His Val Trp Val Gly Tyr Thr Gly Asn
                    245                 250                 255

Ser Gly Gln Arg Ile Tyr Leu Pro Val Arg Thr Trp Asn Lys Ser Thr
                    260                 265                 270

Asn Thr Leu Gly Val Leu Trp Gly Thr Ile Lys
                    275                 280

<210> SEQ ID NO 4
<211> LENGTH: 643
<212> TYPE: PRT
<213> ORGANISM: Artificial Sequence
<220> FEATURE:
<223> OTHER INFORMATION: Chimeric of Staphylococcus epidermidis
      autolysin amidase domain and Staphylococcus simulans
      metalloendopeptidase Lysostaphin CWT domain

<400> SEQUENCE: 4

Met Val Ser Ser Gln Lys Thr Ser Ser Leu Pro Lys Tyr Thr Pro Lys
  1               5                  10                  15

Val Asn Ser Ser Ile Asn Asn Tyr Ile Arg Lys Lys Asn Met Lys Ala
                 20                  25                  30

Pro Arg Ile Glu Glu Asp Tyr Thr Ser Tyr Phe Pro Lys Tyr Gly Tyr
             35                  40                  45

Arg Asn Gly Val Gly Arg Pro Glu Gly Ile Val Val His Asp Thr Ala
 50                  55                  60

Asn Asp Asn Ser Thr Ile Asp Gly Glu Ile Ala Phe Met Lys Arg Asn
 65                  70                  75                  80

Tyr Thr Asn Ala Phe Val His Ala Phe Val Asp Gly Asn Arg Ile Ile
                 85                  90                  95

Glu Thr Ala Pro Thr Asp Tyr Leu Ser Trp Gly Ala Gly Pro Tyr Gly
                100                 105                 110

-continued

```
Asn Gln Arg Phe Ile Asn Val Glu Ile Val His Thr His Asp Tyr Asp
        115                 120                 125

Ser Phe Ala Arg Ser Met Asn Asn Tyr Ala Asp Tyr Ala Ala Thr Gln
130                 135                 140

Leu Gln Tyr Tyr Asn Leu Lys Pro Asp Ser Ala Glu Asn Asp Gly Arg
145                 150                 155                 160

Gly Thr Val Trp Thr His Ala Ala Ile Ser Asn Phe Leu Gly Gly Thr
                165                 170                 175

Asp His Ala Asp Pro His Gln Tyr Leu Arg Ser His Asn Tyr Ser Tyr
                180                 185                 190

Ala Glu Leu Tyr Asp Leu Ile Tyr Glu Lys Tyr Leu Ile Lys Thr Lys
                195                 200                 205

Gln Val Ala Pro Trp Gly Thr Thr Ser Thr Lys Pro Ser Gln Pro Ser
        210                 215                 220

Lys Pro Ser Gly Gly Thr Asn Asn Lys Leu Thr Val Ser Ala Asn Arg
225                 230                 235                 240

Gly Val Ala Gln Ile Lys Pro Thr Asn Asn Gly Leu Tyr Thr Thr Val
                245                 250                 255

Tyr Asp Ser Lys Gly His Lys Thr Asp Gln Val Gln Lys Thr Leu Ser
                260                 265                 270

Val Thr Lys Thr Ala Thr Leu Gly Asn Asn Lys Phe Tyr Leu Val Glu
        275                 280                 285

Asp Tyr Asn Ser Gly Lys Lys Tyr Gly Trp Val Lys Gln Gly Asp Val
        290                 295                 300

Val Tyr Asn Thr Ala Lys Ala Pro Val Lys Val Asn Gln Thr Tyr Asn
305                 310                 315                 320

Val Lys Ala Gly Ser Thr Leu Tyr Thr Val Pro Trp Gly Thr Pro Lys
                325                 330                 335

Gln Val Ala Ser Lys Val Ser Gly Thr Gly Asn Gln Thr Phe Lys Ala
                340                 345                 350

Thr Lys Gln Gln Gln Ile Asp Lys Ala Thr Tyr Leu Tyr Gly Thr Val
        355                 360                 365

Asn Gly Lys Ser Gly Trp Ile Ser Lys Tyr Tyr Leu Thr Thr Ala Ser
        370                 375                 380

Lys Pro Ser Asn Pro Thr Lys Pro Ser Thr Asn Asn Gln Leu Thr Val
385                 390                 395                 400

Ala Gly Gln Thr Ile His Tyr Asp Glu Val Met Lys Gln Asp Gly His
                405                 410                 415

Thr Asn Asn Ser Gly Val Ala Gln Ile Asn Ala Lys Asn Ser Gly Leu
                420                 425                 430

Tyr Thr Thr Val Tyr Asp Thr Lys Gly Lys Thr Thr Asn Gln Ile Gln
        435                 440                 445

Arg Thr Leu Ser Val Thr Lys Ala Ala Thr Leu Gly Asp Lys Lys Phe
450                 455                 460

Tyr Leu Val Gly Asp Tyr Asn Thr Gly Thr Asn Tyr Gly Trp Val Lys
465                 470                 475                 480

Gln Asp Glu Val Ile Tyr Asn Thr Ala Lys Ser Pro Val Lys Ile Asn
                485                 490                 495

Gln Thr Tyr Asn Val Lys Pro Gly Val Lys Leu His Thr Val Pro Trp
                500                 505                 510

Gly Thr Tyr Asn Gln Val Ala Gly Thr Val Ser Gly Lys Gly Asp Gln
        515                 520                 525
```

Thr Phe Lys Ala Thr Lys Gln Gln Ile Asp Lys Ala Thr Tyr Leu
530                 535                 540

Tyr Gly Thr Val Asn Gly Lys Ser Gly Trp Ile Ser Lys Tyr Tyr Leu
545                 550                 555                 560

Leu Gln Thr Pro Asn Thr Gly Trp Lys Thr Asn Lys Tyr Gly Thr Leu
            565                 570                 575

Tyr Lys Ser Glu Ser Ala Ser Phe Thr Pro Asn Thr Asp Ile Ile Thr
            580                 585                 590

Arg Thr Thr Gly Pro Phe Arg Ser Met Pro Gln Ser Gly Val Leu Lys
            595                 600                 605

Val Trp Val Gly Tyr Thr Gly Asn Ser Gly Gln Arg Ile Tyr Leu Pro
610                 615                 620

Val Arg Thr Trp Asn Lys Ser Thr Asn Thr Leu Gly Val Leu Trp Gly
625                 630                 635                 640

Thr Ile Lys

<210> SEQ ID NO 5
<211> LENGTH: 28
<212> TYPE: DNA
<213> ORGANISM: Artificial Sequence
<220> FEATURE:
<223> OTHER INFORMATION: TW-Endo-NcoI-F PCR Primer

<400> SEQUENCE: 5
ctagccatgg aaaccctgaa acaagcag                                      28

<210> SEQ ID NO 6
<211> LENGTH: 41
<212> TYPE: DNA
<213> ORGANISM: Artificial Sequence
<220> FEATURE:
<223> OTHER INFORMATION: TW-Endo-PstI-R PCR Primer

<400> SEQUENCE: 6
acatgctgca gaaccatatt gtaattaata ttagttctat c                       41

<210> SEQ ID NO 7
<211> LENGTH: 36
<212> TYPE: DNA
<213> ORGANISM: Artificial Sequence
<220> FEATURE:
<223> OTHER INFORMATION: NM3-CBD-PstI-F PCR Primer

<400> SEQUENCE: 7
acatgctgca gggtaaatct gcaagtaaaa taacag                             36

<210> SEQ ID NO 8
<211> LENGTH: 35
<212> TYPE: DNA
<213> ORGANISM: Artificial Sequence
<220> FEATURE:
<223> OTHER INFORMATION: NM3-CBD-Hind-R PCR Primer

<400> SEQUENCE: 8
cccaagctta aaacacttct ttcacaatca atctc                              35

<210> SEQ ID NO 9
<211> LENGTH: 42
<212> TYPE: DNA
<213> ORGANISM: Artificial Sequence
<220> FEATURE:
<223> OTHER INFORMATION: NM3-Lys-Xba-F PCR Primer

```
<400> SEQUENCE: 9
ctagtctaga ggtggaataa tgaaaacata cagtgaagca ag                               42

<210> SEQ ID NO 10
<211> LENGTH: 34
<212> TYPE: DNA
<213> ORGANISM: Artificial Sequence
<220> FEATURE:
<223> OTHER INFORMATION: NM3-FWD PCR Primer

<400> SEQUENCE: 10
catgccatgg gtaaatctgc aagtaaaata acag                                       34

<210> SEQ ID NO 11
<211> LENGTH: 35
<212> TYPE: DNA
<213> ORGANISM: Artificial Sequence
<220> FEATURE:
<223> OTHER INFORMATION: NM3-REV PCR Primer

<400> SEQUENCE: 11
cccaagctta aaacacttct ttcacaatca atctc                                      35

<210> SEQ ID NO 12
<211> LENGTH: 467
<212> TYPE: PRT
<213> ORGANISM: Staphylococcus phage Twort

<400> SEQUENCE: 12
```

Met Lys Thr Leu Lys Gln Ala Glu Ser Tyr Ile Lys Ser Lys Val Asn
1               5                   10                  15

Thr Gly Thr Asp Phe Asp Gly Leu Tyr Gly Tyr Gln Cys Met Asp Leu
            20                  25                  30

Ala Val Asp Tyr Ile Tyr His Val Thr Asp Gly Lys Ile Arg Met Trp
        35                  40                  45

Gly Asn Ala Lys Asp Ala Ile Asn Asn Ser Phe Gly Gly Thr Ala Thr
    50                  55                  60

Val Tyr Lys Asn Tyr Pro Ala Phe Arg Pro Lys Tyr Gly Asp Val Val
65                  70                  75                  80

Val Trp Thr Thr Gly Asn Phe Ala Thr Tyr Gly His Ile Ala Ile Val
                85                  90                  95

Thr Asn Pro Asp Pro Tyr Gly Asp Leu Gln Tyr Val Thr Val Leu Glu
            100                 105                 110

Gln Asn Trp Asn Gly Asn Gly Ile Tyr Lys Thr Glu Leu Ala Thr Ile
        115                 120                 125

Arg Thr His Asp Tyr Thr Gly Ile Thr His Phe Ile Arg Pro Asn Phe
    130                 135                 140

Ala Thr Glu Ser Ser Val Lys Lys Lys Asp Thr Lys Lys Pro Lys
145                 150                 155                 160

Pro Ser Asn Arg Asp Gly Ile Asn Lys Asp Lys Ile Val Tyr Asp Arg
                165                 170                 175

Thr Asn Ile Asn Tyr Asn Met Val Lys Arg Gly Tyr Asn Pro Val Gly
            180                 185                 190

Val Ile Leu His Asn Asp Ala Gly Ser Met Thr Gly Leu Gln Tyr Lys
        195                 200                 205

Asn Asn Leu Gln Asn Ala Gly Tyr Asn Arg Trp Ala Gln Gly Ile Ala
    210                 215                 220

His Ser Tyr Ile Ser Glu Gly Gln Val Trp Gln Ala Leu Gly Glu Ser

```
            225                 230                 235                 240
Arg Ile Ala Trp His Cys Ala Asn Gln Trp Gly Asn Lys Asn Leu Tyr
            245                 250                 255
Gly Ile Glu Ile Cys Gln Ser Met Thr Ala Ser Asp Glu Gln Phe Leu
            260                 265                 270
Lys Asn Glu Gln Thr Ala Phe Tyr Glu Ala Ser Arg Met Leu Lys Lys
            275                 280                 285
Trp Gly Leu Lys Pro Asp Lys Asn Thr Val Arg Leu His Met Glu Tyr
            290                 295                 300
Tyr Gln Thr Ala Cys Pro His Arg Ser Met Lys Leu His Val Gly Lys
305                 310                 315                 320
Asp Pro Thr Lys Thr Ser Ile Thr Gln Ala Asp Ile Glu Lys Leu Lys
            325                 330                 335
Glu Tyr Phe Ile Lys Gln Ile Lys Met Tyr Tyr Glu Gly Lys Thr Pro
            340                 345                 350
Val Pro Thr Val Val Asn Gln Lys Ala Lys Thr Lys Pro Val Lys Gln
            355                 360                 365
Ser Ser Thr Ser Gly Trp Asn Val Asn Asn Tyr Gly Thr Tyr Tyr Lys
370                 375                 380
Ser Glu Ser Ala Thr Phe Lys Cys Thr Ala Arg Gln Gly Ile Val Thr
385                 390                 395                 400
Arg Tyr Thr Gly Pro Phe Thr Thr Cys Pro Gln Ala Gly Val Leu Tyr
            405                 410                 415
Tyr Gly Gln Ser Val Thr Tyr Asp Thr Val Cys Lys Gln Asp Gly Tyr
            420                 425                 430
Val Trp Ile Ser Trp Thr Thr Asn Gly Gly Gln Asp Val Trp Met Pro
            435                 440                 445
Val Arg Thr Trp Asp Lys Asn Thr Asp Ile Met Gly Gln Leu Trp Gly
            450                 455                 460
Asp Ile Tyr
465

<210> SEQ ID NO 13
<211> LENGTH: 283
<212> TYPE: PRT
<213> ORGANISM: Artificial Sequence
<220> FEATURE:
<223> OTHER INFORMATION: Chimeric of Bacillus-specific phage lysin

<400> SEQUENCE: 13

Met Gly Tyr Ile Val Asp Met Ser Lys Trp Asn Gly Ser Pro Asp Trp
1               5                   10                  15
Asp Thr Ala Lys Gly Gln Leu Asp Leu Val Ile Ala Arg Val Gln Asp
            20                  25                  30
Gly Ser Asn Tyr Val Asp Pro Val Tyr Lys Asp Tyr Val Ala Ala Met
        35                  40                  45
Lys Ala Arg Asn Ile Pro Phe Gly Ser Tyr Ala Phe Cys Arg Phe Val
    50                  55                  60
Ser Val Glu Asp Ala Lys Val Glu Ala Arg Asp Phe Trp Asn Arg Gly
65              70                  75                  80
Asp Lys Asp Ser Leu Phe Trp Val Ala Asp Val Glu Val Thr Thr Met
                85                  90                  95
Ser Asp Met Arg Ala Gly Thr Gln Ala Phe Ile Asp Glu Leu Tyr Arg
            100                 105                 110
Leu Gly Ala Lys Lys Val Gly Leu Tyr Val Gly His His Lys Tyr Glu
```

```
            115                 120                 125
Glu Phe Gly Ala Ala Gln Ile Lys Cys Asp Phe Thr Trp Ile Pro Arg
        130                 135                 140
Tyr Gly Ala Lys Pro Ala Tyr Pro Cys Asp Leu Trp Gln Tyr Asp Glu
145                 150                 155                 160
Tyr Gly Gln Val Pro Gly Ile Gly Lys Cys Asp Leu Asn Arg Leu Asn
                165                 170                 175
Gly Asp Lys Ser Leu Asp Trp Phe Thr Gly Lys Gly Glu Glu Ala Val
            180                 185                 190
Gln Trp Asn Val Asn Asn Tyr Gly Thr Tyr Lys Ser Glu Ser Ala
        195                 200                 205
Val Phe Thr Leu Asp Arg Thr Ile Asn Leu Arg Thr Ala Pro Phe Pro
210                 215                 220
Thr Ala Pro Leu Ile Ala Gln Leu Asn Ala Gly Asp Asn Val Thr Tyr
225                 230                 235                 240
Asp Gly Tyr Gly Tyr Glu Lys Asp Gly Tyr Val Trp Leu Arg Gln Asn
                245                 250                 255
Arg Gly Asn Gly Asn Tyr Gly Tyr Ile Ala Ser Gly Glu Thr Lys Asn
            260                 265                 270
Gly Gln Arg Ile Ser Thr Trp Gly Thr Phe Lys
        275                 280
```

<210> SEQ ID NO 14
<211> LENGTH: 287
<212> TYPE: PRT
<213> ORGANISM: Artificial Sequence
<220> FEATURE:
<223> OTHER INFORMATION: Cimeric of Bacillus-specific phage lysin PlyB
      catalytic domain and Staphylococcus aureus bacteriophage Twort
      domain

<400> SEQUENCE: 14

```
Met Gly Tyr Ile Val Asp Met Ser Lys Trp Asn Gly Ser Pro Asp Trp
1               5                   10                  15
Asp Thr Ala Lys Gly Gln Leu Asp Leu Val Ile Ala Arg Val Gln Asp
            20                  25                  30
Gly Ser Asn Tyr Val Asp Pro Val Tyr Lys Asp Tyr Val Ala Ala Met
        35                  40                  45
Lys Ala Arg Asn Ile Pro Phe Gly Ser Tyr Ala Phe Cys Arg Phe Val
50                  55                  60
Ser Val Glu Asp Ala Lys Val Glu Ala Arg Asp Phe Trp Asn Arg Gly
65                  70                  75                  80
Asp Lys Asp Ser Leu Phe Trp Val Ala Asp Val Glu Val Thr Thr Met
                85                  90                  95
Ser Asp Met Arg Ala Gly Thr Gln Ala Phe Ile Asp Glu Leu Tyr Arg
            100                 105                 110
Leu Gly Ala Lys Lys Val Gly Leu Tyr Val Gly His His Lys Tyr Glu
        115                 120                 125
Glu Phe Gly Ala Ala Gln Ile Lys Cys Asp Phe Thr Trp Ile Pro Arg
    130                 135                 140
Tyr Gly Ala Lys Pro Ala Tyr Pro Cys Asp Leu Trp Gln Tyr Asp Glu
145                 150                 155                 160
Tyr Gly Gln Val Pro Gly Ile Gly Lys Cys Asp Leu Asn Arg Leu Asn
                165                 170                 175
Gly Asp Lys Ser Leu Asp Trp Phe Thr Gly Lys Gly Glu Glu Ala Val
            180                 185                 190
```

Gln Trp Asn Val Asn Asn Tyr Gly Thr Tyr Tyr Lys Ser Glu Ser Ala
            195                 200                 205

Thr Phe Lys Cys Thr Ala Arg Gln Gly Ile Val Thr Arg Tyr Thr Gly
            210                 215                 220

Pro Phe Thr Thr Cys Pro Gln Ala Gly Val Leu Tyr Tyr Gly Gln Ser
225                 230                 235                 240

Val Thr Tyr Asp Thr Val Cys Lys Gln Asp Gly Tyr Val Trp Ile Ser
                245                 250                 255

Trp Thr Thr Asn Gly Gly Gln Asp Val Trp Met Pro Val Arg Thr Trp
            260                 265                 270

Asp Lys Asn Thr Asp Ile Met Gly Gln Leu Trp Gly Asp Ile Tyr
            275                 280                 285

<210> SEQ ID NO 15
<211> LENGTH: 292
<212> TYPE: PRT
<213> ORGANISM: Artificial Sequence
<220> FEATURE:
<223> OTHER INFORMATION: Chimeric of Bacillus-specific phage lysin PlyB
      catalytic domain and Staphylococcus simulans metalloendopeptidase
      Lysostaphin CWT domain

<400> SEQUENCE: 15

Met Gly Tyr Ile Val Asp Met Ser Lys Trp Asn Gly Ser Pro Asp Trp
1               5                   10                  15

Asp Thr Ala Lys Gly Gln Leu Asp Leu Val Ile Ala Arg Val Gln Asp
            20                  25                  30

Gly Ser Asn Tyr Val Asp Pro Val Tyr Lys Asp Tyr Val Ala Ala Met
        35                  40                  45

Lys Ala Arg Asn Ile Pro Phe Gly Ser Tyr Ala Phe Cys Arg Phe Val
50                  55                  60

Ser Val Glu Asp Ala Lys Val Glu Ala Arg Asp Phe Trp Asn Arg Gly
65                  70                  75                  80

Asp Lys Asp Ser Leu Phe Trp Val Ala Asp Val Glu Val Thr Thr Met
                85                  90                  95

Ser Asp Met Arg Ala Gly Thr Gln Ala Phe Ile Asp Glu Leu Tyr Arg
            100                 105                 110

Leu Gly Ala Lys Lys Val Gly Leu Tyr Val Gly His His Lys Tyr Glu
        115                 120                 125

Glu Phe Gly Ala Ala Gln Ile Lys Cys Asp Phe Thr Trp Ile Pro Arg
    130                 135                 140

Tyr Gly Ala Lys Pro Ala Tyr Pro Cys Asp Leu Trp Gln Tyr Asp Glu
145                 150                 155                 160

Tyr Gly Gln Val Pro Gly Ile Gly Lys Cys Asp Leu Asn Arg Leu Asn
                165                 170                 175

Gly Asp Lys Ser Leu Asp Trp Phe Thr Gly Lys Gly Glu Glu Ala Val
            180                 185                 190

Gln Leu Gln Thr Pro Asn Thr Gly Trp Lys Thr Asn Lys Tyr Gly Thr
        195                 200                 205

Leu Tyr Lys Ser Glu Ser Ala Ser Phe Thr Pro Asn Thr Asp Ile Ile
    210                 215                 220

Thr Arg Thr Thr Gly Pro Phe Arg Ser Met Pro Gln Ser Gly Val Leu
225                 230                 235                 240

Lys Ala Gly Gln Thr Ile His Tyr Asp Glu Val Met Lys Gln Asp Gly
                245                 250                 255

His Val Trp Val Gly Tyr Thr Gly Asn Ser Gly Gln Arg Ile Tyr Leu
            260                 265                 270

Pro Val Arg Thr Trp Asn Lys Ser Thr Asn Thr Leu Gly Val Leu Trp
            275                 280                 285

Gly Thr Ile Lys
            290

<210> SEQ ID NO 16
<211> LENGTH: 658
<212> TYPE: PRT
<213> ORGANISM: Artificial Sequence
<220> FEATURE:
<223> OTHER INFORMATION: Chimeric of Staphylococcus epidermidis
      autolysin amidase domain and Staphylococcus aureus phage pniNM3
      CWT domain

<400> SEQUENCE: 16

Met Val Ser Ser Gln Lys Thr Ser Ser Leu Pro Lys Tyr Thr Pro Lys
1               5                   10                  15

Val Asn Ser Ser Ile Asn Asn Tyr Ile Arg Lys Lys Asn Met Lys Ala
            20                  25                  30

Pro Arg Ile Glu Glu Asp Tyr Thr Ser Tyr Phe Pro Lys Tyr Gly Tyr
        35                  40                  45

Arg Asn Gly Val Gly Arg Pro Glu Gly Ile Val Val His Asp Thr Ala
    50                  55                  60

Asn Asp Asn Ser Thr Ile Asp Gly Glu Ile Ala Phe Met Lys Arg Asn
65                  70                  75                  80

Tyr Thr Asn Ala Phe Val His Ala Phe Val Asp Gly Asn Arg Ile Ile
                85                  90                  95

Glu Thr Ala Pro Thr Asp Tyr Leu Ser Trp Gly Ala Gly Pro Tyr Gly
            100                 105                 110

Asn Gln Arg Phe Ile Asn Val Glu Ile Val His Thr His Asp Tyr Asp
        115                 120                 125

Ser Phe Ala Arg Ser Met Asn Asn Tyr Ala Asp Tyr Ala Ala Thr Gln
    130                 135                 140

Leu Gln Tyr Tyr Asn Leu Lys Pro Asp Ser Ala Glu Asn Asp Gly Arg
145                 150                 155                 160

Gly Thr Val Trp Thr His Ala Ala Ile Ser Asn Phe Leu Gly Gly Thr
                165                 170                 175

Asp His Ala Asp Pro His Gln Tyr Leu Arg Ser His Asn Tyr Ser Tyr
            180                 185                 190

Ala Glu Leu Tyr Asp Leu Ile Tyr Glu Lys Tyr Leu Ile Lys Thr Lys
        195                 200                 205

Gln Val Ala Pro Trp Gly Thr Thr Ser Thr Lys Pro Ser Gln Pro Ser
    210                 215                 220

Lys Pro Ser Gly Gly Thr Asn Asn Lys Leu Thr Val Ser Ala Asn Arg
225                 230                 235                 240

Gly Val Ala Gln Ile Lys Pro Thr Asn Asn Gly Leu Tyr Thr Thr Val
                245                 250                 255

Tyr Asp Ser Lys Gly His Lys Thr Asp Gln Val Gln Lys Thr Leu Ser
            260                 265                 270

Val Thr Lys Thr Ala Thr Leu Gly Asn Asn Lys Phe Tyr Leu Val Glu
        275                 280                 285

Asp Tyr Asn Ser Gly Lys Lys Tyr Gly Trp Val Lys Gln Gly Asp Val
    290                 295                 300

Val Tyr Asn Thr Ala Lys Ala Pro Val Lys Val Asn Gln Thr Tyr Asn

```
            305                 310                 315                 320
Val Lys Ala Gly Ser Thr Leu Tyr Thr Val Pro Trp Gly Thr Pro Lys
                325                 330                 335

Gln Val Ala Ser Lys Val Ser Gly Thr Gly Asn Gln Thr Phe Lys Ala
                340                 345                 350

Thr Lys Gln Gln Gln Ile Asp Lys Ala Thr Tyr Leu Tyr Gly Thr Val
                355                 360                 365

Asn Gly Lys Ser Gly Trp Ile Ser Lys Tyr Tyr Leu Thr Thr Ala Ser
            370                 375                 380

Lys Pro Ser Asn Pro Thr Lys Pro Ser Thr Asn Asn Gln Leu Thr Val
385                 390                 395                 400

Thr Asn Asn Ser Gly Val Ala Gln Ile Asn Ala Lys Asn Ser Gly Leu
                405                 410                 415

Tyr Thr Thr Val Tyr Asp Thr Lys Gly Lys Thr Thr Asn Gln Ile Gln
                420                 425                 430

Arg Thr Leu Ser Val Thr Lys Ala Ala Thr Leu Gly Asp Lys Lys Phe
                435                 440                 445

Tyr Leu Val Gly Asp Tyr Asn Thr Gly Thr Asn Tyr Gly Trp Val Lys
            450                 455                 460

Gln Asp Glu Val Ile Tyr Asn Thr Ala Lys Ser Pro Val Lys Ile Asn
465                 470                 475                 480

Gln Thr Tyr Asn Val Lys Pro Gly Val Lys Leu His Thr Val Pro Trp
                485                 490                 495

Gly Thr Tyr Asn Gln Val Ala Gly Thr Val Ser Gly Lys Gly Asp Gln
                500                 505                 510

Thr Phe Lys Ala Thr Lys Gln Gln Gln Ile Asp Lys Ala Thr Tyr Leu
                515                 520                 525

Tyr Gly Thr Val Asn Gly Lys Ser Gly Trp Ile Ser Lys Tyr Tyr Leu
            530                 535                 540

Leu Gln Gly Leu Met Asn Lys Ile Thr Asn Lys Val Lys Pro Pro Ala
545                 550                 555                 560

Gln Lys Ala Val Gly Lys Ser Ala Ser Lys Ile Thr Val Gly Ser Lys
                565                 570                 575

Ala Pro Tyr Asn Leu Lys Trp Ser Lys Gly Ala Tyr Phe Asn Ala Lys
                580                 585                 590

Ile Asp Gly Leu Gly Ala Thr Ser Ala Thr Arg Tyr Gly Asp Asn Arg
            595                 600                 605

Thr Asn Tyr Arg Phe Asp Val Gly Gln Ala Val Tyr Ala Pro Gly Thr
            610                 615                 620

Leu Ile Tyr Val Phe Glu Ile Ile Asp Gly Trp Cys Arg Ile Tyr Trp
625                 630                 635                 640

Asn Asn His Asn Glu Trp Ile Trp His Glu Arg Leu Ile Val Lys Glu
                645                 650                 655

Val Phe

<210> SEQ ID NO 17
<211> LENGTH: 280
<212> TYPE: PRT
<213> ORGANISM: Artificial Sequence
<220> FEATURE:
<223> OTHER INFORMATION: Chmeric of Staphylococcus aureus bacteriophage
      Twort domain and Staphylococcus aureus phage phiNM3 CWT domain

<400> SEQUENCE: 17

Met Glu Thr Leu Lys Gln Ala Glu Ser Tyr Ile Lys Ser Lys Val Asn
```

-continued

```
1               5                   10                  15

Thr Gly Thr Asp Phe Asp Gly Leu Tyr Gly Tyr Gln Cys Met Asp Leu
            20                  25                  30

Ala Val Asp Tyr Ile Tyr His Val Thr Asp Gly Lys Ile Arg Met Trp
            35                  40                  45

Gly Asn Ala Lys Asp Ala Ile Asn Asn Ser Phe Gly Gly Thr Ala Thr
            50                  55                  60

Val Tyr Lys Asn Tyr Pro Ala Phe Arg Pro Lys Tyr Gly Asp Val Val
65                      70                  75                  80

Val Trp Thr Thr Gly Asn Phe Ala Thr Tyr Gly His Ile Ala Ile Val
                85                  90                  95

Thr Asn Pro Asp Pro Tyr Gly Asp Leu Gln Tyr Val Thr Val Leu Glu
            100                 105                 110

Gln Asn Trp Asn Gly Asn Gly Ile Tyr Lys Thr Glu Leu Ala Thr Ile
            115                 120                 125

Arg Thr His Asp Tyr Thr Gly Ile Thr His Phe Ile Arg Pro Asn Phe
            130                 135                 140

Ala Thr Glu Ser Ser Val Lys Lys Lys Asp Thr Lys Lys Lys Pro Lys
145                 150                 155                 160

Pro Ser Asn Arg Asp Pro Ile Asn Lys Asp Lys Ile Val Tyr Asp Arg
                165                 170                 175

Thr Asn Ile Asn Tyr Asn Met Val Leu Gln Gly Lys Ser Ala Ser Lys
            180                 185                 190

Ile Thr Val Gly Ser Lys Ala Pro Tyr Asn Leu Lys Trp Ser Lys Gly
            195                 200                 205

Ala Tyr Phe Asn Ala Lys Ile Asp Gly Leu Gly Ala Thr Ser Ala Thr
210                 215                 220

Arg Tyr Gly Asp Asn Arg Thr Asn Tyr Arg Phe Asp Val Gly Gln Ala
225                 230                 235                 240

Val Tyr Ala Pro Gly Thr Leu Ile Tyr Val Phe Glu Ile Ile Asp Gly
                245                 250                 255

Trp Cys Arg Ile Tyr Trp Asn Asn His Asn Glu Trp Ile Trp His Glu
            260                 265                 270

Arg Leu Ile Val Lys Glu Val Phe
            275                 280
```

CHIMERIC BACTERIOPHAGE LYSIN WITH ACTIVITY AGAINST STAPHYLOCOCCI BACTERIA

CROSS-REFERENCES TO RELATED APPLICATIONS

The present application is a Continuation of U.S. Non-Provisional application Ser. No. 14/480,822 filed Sep. 9, 2014, now U.S. Pat. No. 10,053,681 issued Aug. 21, 2018, which in turn, is a Continuation of National Stage application Ser. No. 13/502,912, filed Jun. 26, 2012, now U.S. Pat. No. 8,840,900 issued Sep. 23, 2014, which claims priority from PCT Application No. PCT/US2009/049349 filed Jul. 1, 2009, which claims the benefit of priority from U.S. Provisional Patent Application No. 61/078,277 filed Jul. 3, 2008. Applicants claim the benefits of 35 U.S.C. § 120 as to the U.S. Non-Provisional applications and the PCT Application and priority under 35 U.S.C. § 119 as to the said U.S. Provisional application, and the entire disclosures of all applications are incorporated herein by reference in their entireties.

FEDERALLY SPONSORED RESEARCH AND DEVELOPMENT

This invention was made with government support under grant number AI11822 awarded by the National Institutes of Health (NIH). The U.S. government may retain certain rights to the invention.

TECHNICAL FIELD

The present disclosure relates to the identification and use of chimeric lytic enzymes to rapidly and specifically detect and kill Staphylococci bacteria, including certain antibiotic-resistant *Staphylococcus aureus* bacterial strains.

BACKGROUND

*Staphylococcus aureus* is an opportunistic pathogen inhabiting human skin and mucous membranes. *S. aureus* is the causative agent of variety of skin and soft tissue infections in humans and serious infections such as pneumonia, meningitis, endocarditis, and osteomyelitis. *S. aureus* exotoxins also cause disease syndromes such as bullous impetigo, scalded skin syndrome, and toxic shock syndrome. Additionally, staphylococci are also among the most common causes of food-borne illness in United States (Fischetti V A, Novick, R. P., Ferretti, J. J., Portnoy, D. A. and Rood, J. I., editor. 2006. Gram-positive pathogens. 2nd ed: ASM Press). *S. aureus* is also a major cause of community- and hospital-acquired (nosocomial) infections. Of the nearly 2 million cases of nosocomial infections in United States, approximately 230,000 cases are caused by *S. aureus* (NNIS. 2003. NNIS report, data summary from January 1992 through June 2003, issued August 2003. American Journal of Infection Control 31:481-498.).

The global appearance of methicillin- and vancomycin-resistant clinical isolates of *S. aureus* has become a serious concern. Currently, 40-60% of nosocomial infections of *S. aureus* are resistant to oxacillin (Massey R C, Horsburgh M J, Lina G, Hook M, Recker M. 2006. The evolution and maintenance of virulence in *Staphylococcus aureus*: a role for host-to-host transmission? Nat Rev Microbiol 4(12):953-8.) and greater than 60% of the isolates are resistant to methicillin (Gill S R, Fouts D E, Archer G L, Mongodin E F, Deboy R T, Ravel J, Paulsen I T, Kolonay J F, Brinkac L, Beanan M and others. 2005. Insights on evolution of virulence and resistance from the complete genome analysis of an early methicillin-resistant *Staphylococcus aureus* strain and a biofilm-producing methicillin-resistant *Staphylococcus epidermidis* strain. J Bacteriol 187(7):2426-38.). Treating infections caused by the drug-resistant *S. aureus* has become increasingly difficult and therefore is a major concern among healthcare professionals. To combat this challenge, development of new and effective antibiotics belonging to different classes are being aggressively pursued. A number of new antimicrobial agents such as linezolid, quinupristing-dalfopristin, daptomycin, tigecyline, new glycopeptides and ceftobiprole have been introduced or are under clinical development (Aksoy D Y, Unal S. 2008. New antimicrobial agents for the treatment of Gram-positive bacterial infections. Clin Microbiol Infect 14(5):411-20.). However, clinical isolates of MRSA (methicillin-resistant *Staphylococcus aureus*) with resistance to these new classes of antibiotics have already been reported (Tsiodras S, Gold H S, Sakoulas G, Eliopoulos G M, Wennersten C, Venkataraman L, Moellering R C, Ferraro M J. 2001. Linezolid resistance in a clinical isolate of *Staphylococcus aureus*. Lancet 358(9277):207-8; Mangili A, Bica I, Snydman D R, Hamer D H. 2005. Daptomycin-resistant, methicillin-resistant *Staphylococcus aureus* bacteremia. Clin Infect Dis 40(7):1058-60; Skiest D J. 2006. Treatment failure resulting from resistance of *Staphylococcus aureus* to daptomycin. J Clin Microbiol 44(2):655-6). Consequently, there is an urgent need to develop novel therapeutic agents or antibiotic alternatives against MRSA.

Bacteriophage endolysins (lysins) are one such class of novel antimicrobial agents that are emerging as novel agents for the prophylactic and therapeutic treatment of bacterial infections. Lysins are cell wall hydrolases that are produced during the infection cycle of double-stranded DNA bacteriophages (or phages) enabling release of progeny virions. Typically, lysins have two distinct functional domains consisting of a catalytic domain for peptidoglycan hydrolysis and a binding domain for recognition of surface moieties on the bacterial cell walls. The catalytic domains are relatively conserved among lysins. The activities of lysins can be classified into two groups based on bond specificity within the peptidoglycan: glycosidases that hydrolyze linkages within the aminosugar moieties and amidases that hydrolyze amide bonds of cross-linking stem peptides. The binding domains however are not conserved among lysins. Hence the binding domain imparts species- and strain-specificity because the binding targets, often carbohydrates associated with the peptidoglycan, display species- or strain-specific distribution (Fischetti V A, Nelson D, Schuch R. 2006. Reinventing phage therapy: are the parts greater than the sum? Nat Biotechnol 24(12):1508-11). The modular architecture of lysins' is an important feature with respect to their development as antimicrobial agents. This enables creation of chimeras by swapping lysin domains and thereby altering binding specificity or enzymatic activity or both (Sheehan M M, Garcia J L, Lopez R, Garcia P. 1996. Analysis of the catalytic domain of the lysin of the lactococcal bacteriophage Tuc2009 by chimeric gene assembling. FEMS Microbiol Lett 140(1):23-8; Lopez R G E, Garcia P, Garcia J L. 1997. The pneumococcal cell wall degrading enzymes: a modular design to create new lysins? Microb Drug Res 3:199-211; Croux C, Ronda C, Lopez R, Garcia J L. 1993. Interchange of functional domains switches enzyme specificity: construction of a chimeric pneumococcal-clostridial cell wall lytic enzyme. Mol Microbiol 9(5):1019-25; Donovan D M, Dong S, Garrett W, Rousseau G M, Moineau S, Pritchard D G. 2006. Peptidoglycan hydrolase fusions maintain their parental specificities. Appl Environ Microbiol 72(4):2988-96).

When applied exogenously, native or recombinant lysins were able to degrade the cell wall of susceptible bacteria and cause rapid cell lysis (Nelson D, Loomis L, Fischetti V A. 2001. Prevention and elimination of upper respiratory colonization of mice by group A streptococci by using a bacteriophage lytic enzyme. Proc Natl Acad Sci USA 98(7):4107-12). Lysins have been developed against a number of Gram-positive pathogens including Group A streptococci (Nelson D, Loomis L, Fischetti V A. 2001. Prevention and elimination of upper respiratory colonization of mice by group A streptococci by using a bacteriophage lytic enzyme. Proc Natl Acad Sci USA 98(7):4107-12), *S. pneumoniae* (Loeffler J M, Nelson D, Fischetti V A. 2001. Rapid killing of *Streptococcus pneumoniae* with a bacteriophage cell wall hydrolase. Science 294(5549):2170-2), *Bacillus anthracis* (Schuch R, Nelson D, Fischetti V A. 2002. A bacteriolytic agent that detects and kills *Bacillus anthracis*. Nature 418 (6900):884-9), enterococci (Yoong P, Schuch R, Nelson D, Fischetti V A. 2004. Identification of a broadly active phage lytic enzyme with lethal activity against antibiotic-resistant *Enterococcus faecalis* and *Enterococcus faecium*. J Bacteriol 186(14):4808-12), Group B streptococci (Cheng Q, Nelson D, Zhu S, Fischetti V A. 2005. Removal of group B streptococci colonizing the vagina and oropharynx of mice with a bacteriophage lytic enzyme. Antimicrob Agents Chemother 49(1):111-7), and *Staphylococcus aureus* (Rashel M, Uchiyama J, Ujihara T, Uehara Y, Kuramoto S, Sugihara S, Yagyu K, Muraoka A, Sugai M, Hiramatsu K and others. 2007. Efficient elimination of multidrug-resistant *Staphylococcus aureus* by cloned lysin derived from bacteriophage phi MR11. J Infect Dis 196(8):1237-47). The activities of most of these lysins have been demonstrated in vitro and in in vivo models. Several unique characteristics of lysin make them attractive antibacterial candidates against Gram-positive pathogens. These include i) rapid antibacterial activity both in vitro and in vivo; ii) very narrow lytic spectrum (species- and strain-specific); iii) very strong binding affinity, typically in the nanomolar range; iv) very low chances of developing resistance since the binding epitopes are essential for viability; v) safe; and vi) relative ease of modification by genetic engineering (Fischetti V A, Nelson D, Schuch R. 2006. Reinventing phage therapy: are the parts greater than the sum? Nat Biotechnol 24(12):1508-11).

Although lysins have been developed against a number of Gram-positive pathogens, there remains a need for a *S. aureus*-specific lysin. Various labs have unsuccessfully attempted to obtain a staphylococcal lysin. The expression of more than twenty different staphylococcal lysins using a variety of techniques have been attempted without success. These include expression of lysin genes in *E. coli* using different expression vectors and conditions, expression in *Bacillus*, yeast and mammalian systems, expression in the presence of chaperones, expression of truncated versions etc. To our knowledge, there is only one report of the successful development of *S. aureus*-specific lysin called MV-L (Rashel M, Uchiyama J, Ujihara T, Uehara Y, Kuramoto S, Sugihara S, Yagyu K, Muraoka A, Sugai M, Hiramatsu K and others. 2007. Efficient elimination of multidrug-resistant *Staphylococcus aureus* by cloned lysin derived from bacteriophage phi MR11. J Infect Dis 196(8):1237-47). MV-L lysin is comprised of two catalytic domains (an endopeptidase and an amidase domain) linked to a single cell wall targeting (CWT) domain, a type of binding domain. Unless otherwise indicated, references herein to a "binding domain" herein include a CWT domain. The MV-L CWT domain, like the staphylolytic enzyme lysostaphin, displays homology to SH3b-like domains. The SH3b-like domains bind to the peptide cross-bridge (the penta Glycine) in the staphylococcal cell wall. There are reports of staphylococcal strains developing resistance at $10^{-6}$ frequencies to lysostaphin by altering their peptide cross-bridges. Therefore, we expect staphylococci to develop resistance at a higher frequency to lysins containing SH3b-like CWT domains including MV-L. There is a need for lytic enzymes capable of specific binding to Staphylococcal bacteria without undesirably high frequencies of lysostaphin resistance, such as *S. aureus*—specific lysins without SH3b-like CWT domains.

SUMMARY

This disclosure describes novel staphylococcal lysins, as well as methods of making and using the lysin. In one example, the genetic engineering of a novel chimeric lysin called ClyS (for chimeric lysin for staphylococci) is described. ClyS is specifically active against susceptible and drug-resistant staphylococci, and was constructed by fusing the catalytic domain of a *Staphylococcus*-specific phage lysin with a unique binding domain from another *Staphylococcus*-specific phage lysin that has no known homologs. ClyS is a soluble Staphylococcal-specific lysin without a SH3b-like CWT domain, but does contain a CWT domain that is believed to recognize a staphylococci-specific surface carbohydrate. Consequently, the frequency by which staphylococcal strains will develop resistance to ClyS may be reduced. Additionally, biochemical characterization of ClyS revealed that the pH and salt spectrum of ClyS is very different from conventional lysins thereby providing unique properties to this chimeric lysin.

Also included within the scope of the present invention are methods of using the binding domain for diagnostic purposes, the method comprising the steps of contacting a sample with a reporter molecule comprising a cell wall target domain comprising the amino acid sequence of SEQ ID NO:1 and a fluorescent reporting moiety bound thereto; and subsequently detecting the presence of the reporter molecule bound to a *Staphylococcus* bacteria within the sample. In certain embodiments, the reporter molecule is a green fluorescent protein.

BRIEF DESCRIPTION OF THE DRAWINGS

FIG. 2B shows the amino acid sequence of the phiNM3 CWT protein (SEQ ID NO:1).

FIG. 3 shows a series of micrographs showing PhiNM3 CWT binding specifically to staphylococci. Purified phiNM3 CWT was labeled with FITC and exposed to 1) *S. aureus;* 2) *B. cereus;* 3) *S. epidermidis;* 4) *E. coli;* 5) Group A *Streptococcus* and 6) mixed suspension of *S. aureus* and *B. cereus* cells. "P" indicates phase-contrast image and "F" indicates fluorescent image.

FIG. 5B shows the amino acid sequence for the AD127 chimeric molecule, described with respect to FIG. 4.

FIGS. 8A-8C (A-C) are thin-section transmission electron micrographs (bars, 200 nm) of *S. aureus* 3 minutes after exposure to 50 U of ClyS. The arrows indicate cytoplasmic membrane extrusions through holes generated in the cell wall by ClyS. Ultimate lysis results in "cell-ghosts" (D) after the loss of cytoplasmic contents (bar, 500 nm).

FIG. 9A is a graph of the activity of ClyS (50 U) tested against *S. aureus* strain 8325-4 in buffers with pH values ranging from 4 and 10 in 15 minute assays. Optical density (filled squares) and viability (filled diamonds) was measured as described in legend of FIG. 6. Fold killing in the viability assay was calculated by dividing the number of viable bacteria after buffer treatment at a particular pH by the number after exposure to ClyS enzyme at the same pH. Final pH readings for each reaction are recorded on the x axis. FIG. 9B is a graph showing the activity of ClyS (50 U) tested against *S. aureus* strain 8325-4 in 20 mM phosphate buffer (pH 7.4) in the presence of different concentrations of NaCl. After 15 minutes samples were assayed for optical density and viability calculated as above.

DETAILED DESCRIPTION

Definitions

Unless otherwise indicated, the certain terms used herein and their applicability to the present disclosure are defined below.

The term "isolated" means at least partially purified from a starting material. The term "purified" means that the biological material has been measurably increased in concentration by any purification process, including by not limited to, column chromatography, HPLC, precipitation, electrophoresis, etc., thereby partially, substantially or completely removing impurities such as precursors or other chemicals involved in preparing the material. Hence, material that is homogenous or substantially homogenous (e.g., yields a single protein signal in a separation procedure such as electrophoresis or chromatography) is included within the meanings of isolated and purified. Skilled artisans will appreciate that the amount of purification necessary will depend upon the use of the material. For example, compositions intended for administration to humans ordinarily must be highly purified in accordance with regulatory standards.

The term "lytic enzyme genetically coded for by a bacteriophage" refers to a polypeptide having at least some lytic activity against the host bacteria.

Variants of "chimeric bacteriophage lysin" are included within the definition of chimeric bacteriophage lysins, and include a functionally active chimeric bacteriophage lysin with killing activity against *Staphylococcus aureus* having at least 50%, 55%, 60%, 65%, 70%, 75%, 80%, 85%, 90%, 95%, 97%, 98%, 99%, or even at least 99.5% amino acid sequence identity with a sequence described herein. For example, the present invention includes chimerical bacteriophage lysins having at least 50%, 55%, 60%, 65%, 70%, 75%, 80%, 85%, 90%, 95%, 97%, 98%, 99%, or even at least 99.5% amino acid sequence identity with the polypeptide sequence of SEQ ID NO:2.

"Percent (%) polypeptide sequence identity" with respect to the lytic enzyme polypeptide sequences identified here is defined as the percentage of amino acid residues in a candidate sequence that are identical with the amino acid residues in the specific lytic enzyme polypeptide sequence, after aligning the sequences and introducing gaps, if necessary, to achieve the maximum percent sequence identity, and not considering any conservative substitutions as part of the sequence identity. Methods for alignment for purposes of determining percent amino acid sequence identity are described below.

Staphylococcal Lysins

Figure 1:
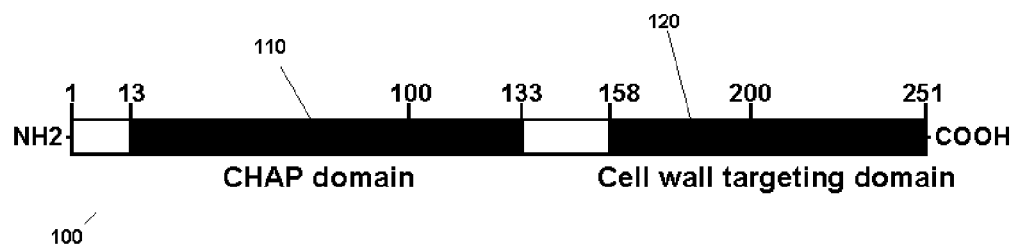
FIG. 1 is a schematic diagram of phiNM3 lysin showing the putative CHAP ("cysteine- and histidine-dependent amidohydrolase/peptidase") and CWT domains. The numbers represent the amino acid positions and the domain limits. The CWT domain of ClyS is indicated in the diagram.

Chimeric bacteriophage lysins with killing activity against S. aureus are described herein. Lysins generally occur in a modular structure. FIG. 1 is a schematic diagram of phiNM3 lysin showing the putative CHAP domain 110 and the CWT domain 120. The numbers represent the amino acid positions and the domain limits. The CWT domain of ClyS is shown as shaded box 120. The N-terminal module consists of a catalytic domain believed to possess the ability to break down the bacterial cell wall of certain bacteria. Enzymatic activities often associated with the catalytic domain are amidases, endopeptidases, glucosamidases and muramidases. The C-terminal module consists of a binding domain that is believed to have an affinity for a carbohydrate epitope on the target bacteria cell wall. The binding domain is believed to determine the specificity of the lysin. The peptide cross-bridge within the staphylococcal peptidoglycan is believed to function as the receptor for the CWT domain of lysostaphin, a staphylolytic enzyme produced by Staphylococcus simulans. The CWT domain of lysostaphin has homology to the SH3b domain suggesting that such lysins might also utilize the peptide cross-bridge as its receptor.

In one embodiment, Staphylococcus-specific binding molecules comprising a CWT domain within staphylococcal lysins are provided that have no known domain homologs. In some embodiments, the binding molecules are lysins. In other embodiments, the binding molecules may be used as diagnostic tools, for example to identify the presence of Staphylococcus bacteria. Preferably, such a CWT domain is provided to recognize a different epitope such as a cell wall-associated carbohydrate instead of the peptide cross-bridge in the staphylococcal cell wall.

In a further embodiment, the ClyS lysine can be used to digest the cell wall of Staphylococcus aureus bacterial strains, which in turn would allow access to the genetic and cytoplasmic material, such as endogenous DNA and RNA, to further identify and sequence the Staphylococcus aureus bacterial strain. It will also release membrane-associated and wall-associated molecules for diagnostic purposes.

Figure 2A:
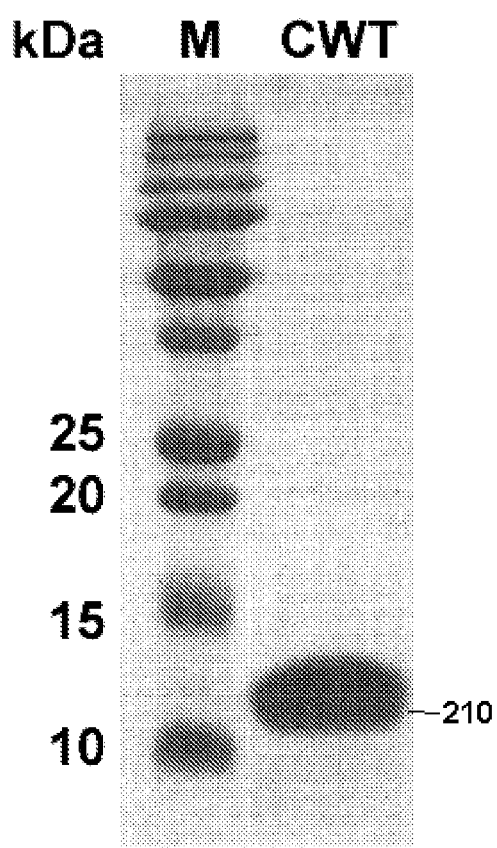
FIG. 2A is a gel showing the purification of phiNM3 CWT. SDS-PAGE and coomassie blue stained gel of phiNM3 CWT purified by anion-exchange chromatography is depicted in the lane marked "CWT." Protein molecular weight markers in kilodaltons (kDa) are shown in the lane marked "M."

Most preferably, the binding molecule is a soluble binding domain of a bacterial lysin comprising a polypeptide including an amino acid sequence providing specific binding to S. aureus, such as SEQ ID NO:1 (phiNM3 CWT domain). For example, the lysin preferably includes the polypeptide sequence of S. aureus phage phiNM3 lysin (SEQ ID NO:1) (protein accession number YP_908849). The phiNM3 lysin CWT domain (SEQ ID NO:1) corresponding to amino acid residues 158-251 was cloned and expressed. The approximately 10-kDa protein of SEQ ID NO:1 was highly soluble and was purified by one-step anion-exchange chromatography to homogeneity. FIG. 2A is an anion exchange gel showing the protein of SEQ ID NO:1 in a second column next to a set of marker proteins in a first column. FIG. 2B shows the amino acid sequence of SEQ ID NO:1. To determine whether the peptide domain of SEQ ID NO:1 displayed Staphylococcus-specific binding, the purified protein was labeled with FITC and exposed to log-phase S. aureus, S. epidermidis and mixed population of S. aureus and Bacillus. Group A streptococci, E. coli and Bacillus cereus were used as controls. More preferably, The FITC-labeled phiNM3 CWT domain bound specifically to S. aureus (FIG. 3-1) and S. epidermidis (FIG. 3-3) cells when present in single or mixed populations (FIG. 3-6) while binding to streptococci (FIG. 3-5), Bacillus (FIG. 3-2) or E. coli (FIG. 3-4) was not observed. PhiNM3 lysin specifically bound to S. aureus (FIG. 3-1) and S. epidermidis (FIG. 3-2) cells when present in single or mixed populations (FIG. 3-3) while binding to streptococci (FIG. 3-4), Bacillus (FIG. 3-5) or E. coli (FIG. 3-6) was not observed.

In one embodiment, the binding molecule comprises a CWT binding domain, such as the amino acid sequence of SEQ ID NO:1, attached to a reporting portion that is detectable to identify the presence of the binding molecule bound to Staphylococcal bacteria. For example, the binding molecule may include the amino acid sequence of SEQ ID NO:1 bound to a fluorescent reporter group, a radioactive reporter group or a heterologous tag that is adapted to bind a fluorescent reporter. The phiNM3 (SEQ ID NO:1) CWT domain may be used as a diagnostic tool for the identification of staphylococcal bacteria. The high affinity binding site may be used in a wide range of assay techniques to detect S. aureus. Such assay methods include radioimmunoassays, gold sol radial immune assays, competitive-binding assays, Western Blot assays and ELISA assays. Such detection assays advantageously utilize a heterogeneous format wherein a binding reaction (SEQ ID NO:1) between a conjugated binding agent comprising (SEQ ID NO:1) and an analyte occurs followed by a wash step to remove unbound conjugated binding agent. For example, gold sol particles may be prepared with protein that comprises the binding region with the binding protein immobilized on the particle surfaces. As binding occurs between the protein and (staphylococcal) bacteria, the particles merge and form a colored product. Analogously, the binding protein may be complexed, preferably covalently with an enzyme such as beta galactosidase, peroxidase, or horseradish peroxidase. After wash, the remaining bound enzyme can be detected by adding a substrate such as a fluorogenic or chemilumigenic substrate. The binding protein may be complexed with any other reagent that can make a signal such as a rare earth fluor and detected by time resolved fluorescence, a radioactive material and detected by radioactivity measurement, green fluorescent protein (GFP) or another fluorescent tag, and detected by fluorescence.

Figure 4:
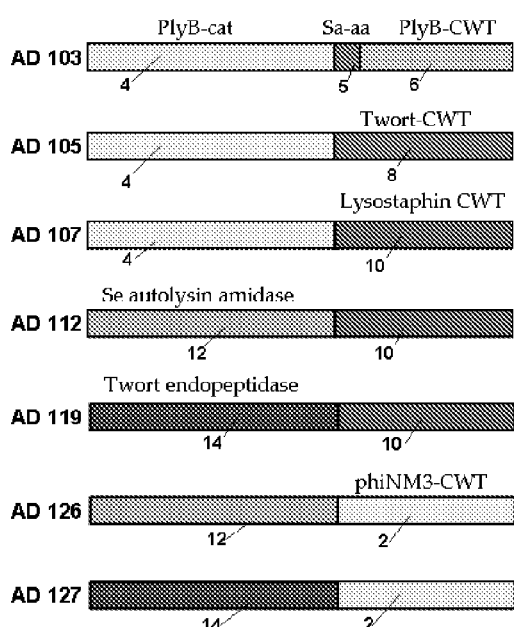
FIG. 4 is a schematic diagram illustrating chimeric lysin development. In particular, FIG. 4 provides schematic diagrams of various chimeric lysins showing their respective domains and the corresponding expression and solubility of the protein and activity against *S. aureus* cells. Similar domains are depicted in the same shading and labeled. PlyB-cat indicates catalytic domain of *Bacillus*-specific lysin PlyB (and is marked with a "4" in the figure); Sa-aa indicates 16 amino acid residues specific for staphylococcal lysins (and is marked with a "5" in the figure); PlyB-CWT indicates CWT domain of PlyB (and is marked with a "6" in the figure); Twort-CWT indicates CWT domain of *S. aureus* phage Twort lysin (and is marked with a "8" in the figure); Lysostaphin CWt indicates CWT domain of lysostaphin (and is marked with a "10" in the figure); and Se autolyin amidase indicates an amidase domain of *S. epidermidis* autolysin (and is marked with a "12" in the figure).

For comparison, FIG. 5B provides the amino acid sequence of SEQ ID NO:3, the AD119 sample discussed with respect to FIG. 4. AD119 (SEQ ID NO:3) comprises the Twort endopeptidase domain joined to the Lysostaphin CWT domain. In contrast to the chimeric compound of SEQ ID NO:2 (AD127), which shares the Twort endopeptidase domain but has the phiNM3 CWT domain (SEQ ID NO:1) in place of the Lysostaphin CWT domain, the AD127 compound was insoluble and exhibited little or no killing activity against S. aureus.

The conjugation of the binding region with a detectable tag may be carried out by synthetic chemistry or a biological process. For example, a DNA sequence coding for the binding region of SEQ ID NO:1 or of the entire lysin of SEQ ID NO:2 can be linked to genetic information that encodes a detectable marker such as green fluorescent protein (GFP)

or an enzyme such as alkaline phosphatase. This could be accomplished by separating the DNA for the binding domain by removing the N-terminal catalytic domain and replacing it in frame with indicator molecules such as green flourescent protein (GFP) and purifying the expressed fusion molecule for the identification of S. aureus. Since the binding domain has a similar binding affinity of an immunoglobulin G molecule, the marked binding domain will effectively identify Staphylococcus aureus with little false positive activity. One also could fuse the GFP molecule or an enzyme at the 5' end of the whole lysin enzyme if necessary, by doing so the enzymatic domain will be at least partly inactivated, still allowing the binding domain to function to bind to its substrate in the bacillus cell wall. Optionally, the isolated binding domain of SEQ ID NO:1 may be separated from the catalytic domain of SEQ ID NO:2 and may be expressed, purified and labeled using a number of fluorescent molecules such as fluorescein isothiocyanate, rhodamine isothiocyanate and others known by skilled artisans. The binding domain may be modified with biotin to allow formation of a biotin-avidin complex after the binding region adheres to the Staphylococcus aureus for identification.

Figure 5A:
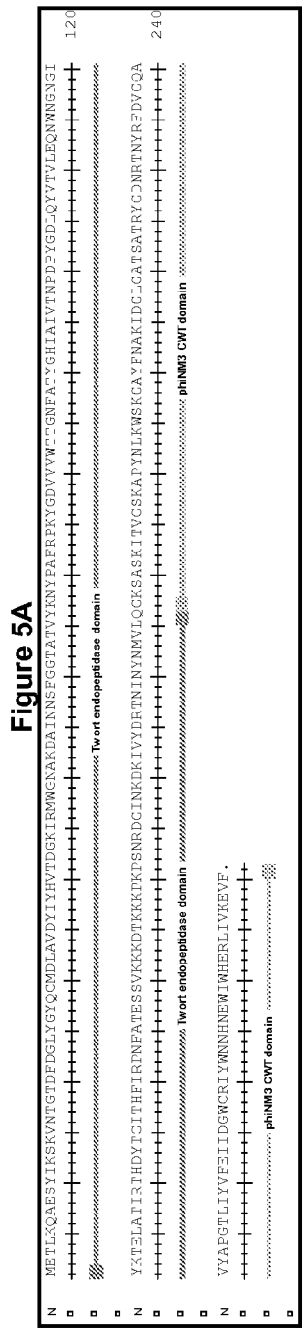
FIG. 5A shows the ClyS protein sequence. The predicted protein sequence of the chimeric protein ClyS showing the Twort endopeptidase catalytic and the phiNM3 CWT domains.
Figure 5C:
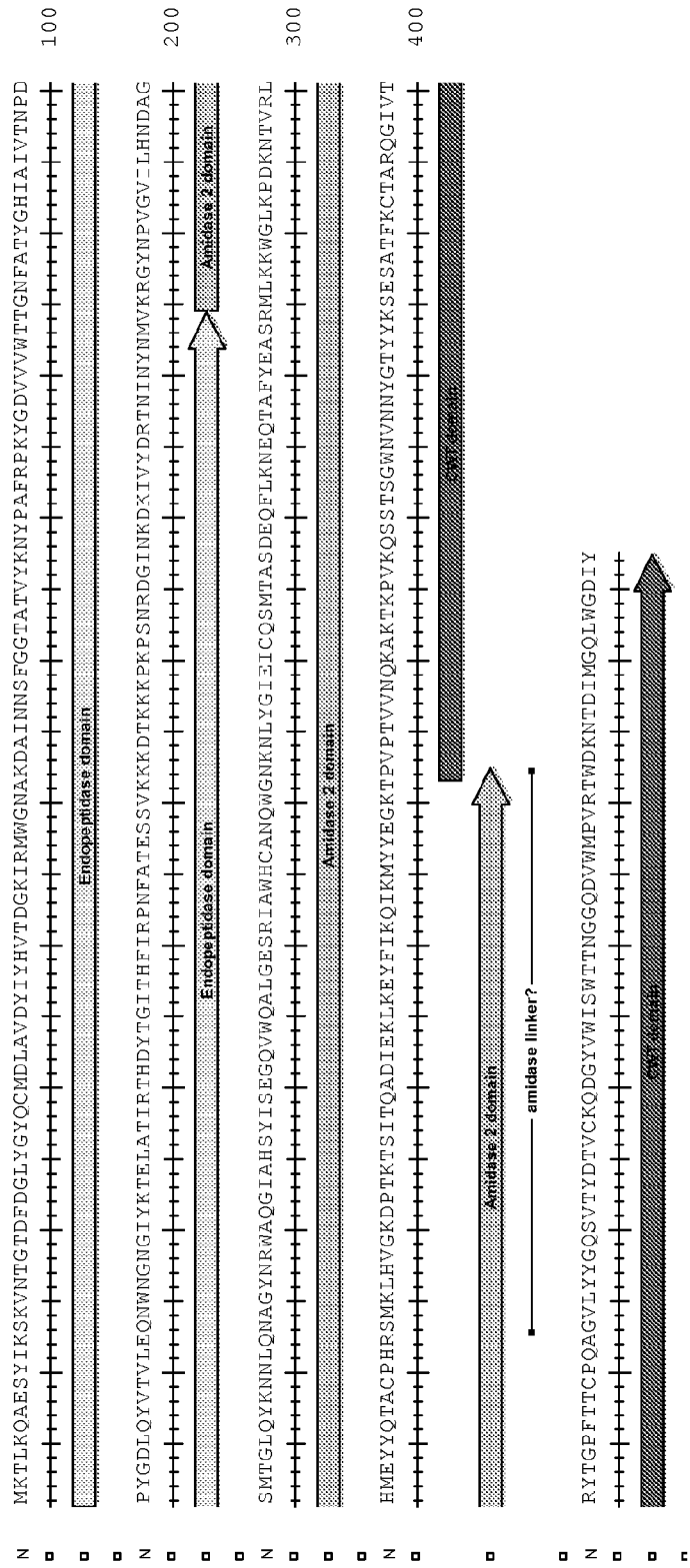
FIG. 5C shows the amino acid sequence for the native (unmodified) Twort lysin (SEQ ID NO: 12).
Figure 6:
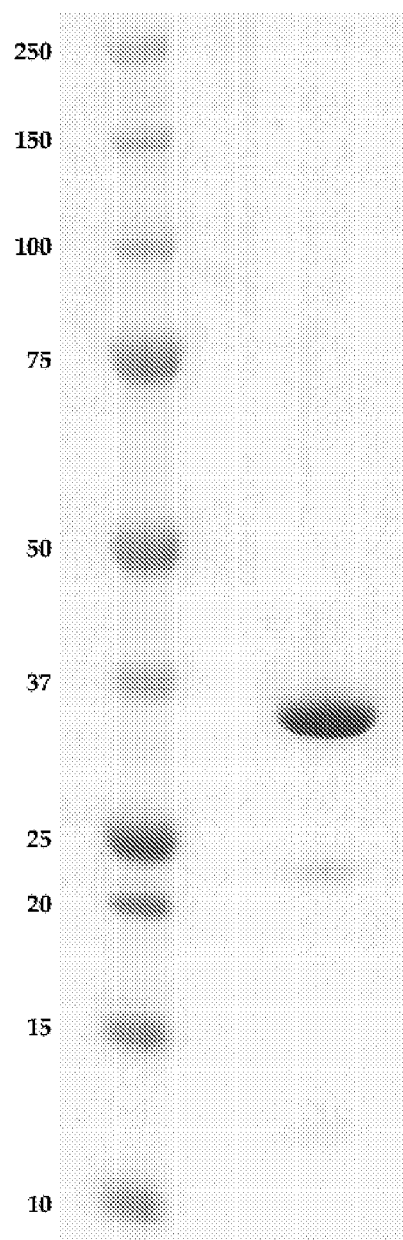
FIG. 6 is a gel showing the purification of ClyS. ClyS was expressed in *E. coli* DH5α cells and purified by cation-exchange chromatography followed by hydroxyapatite chromatography. Purified sample (10 micrograms) was separated by SDS-PAGE and stained by Coomassie blue (right hand lane). Protein molecular weight markers in kilodaltons (kDa) are shown in the left hand lane.

In another embodiment, the lysin is a chimeric protein that comprises an endopeptidase domain of the S. aureus Twort lysin upstream of the phiNM3 CWT domain (SEQ ID NO:1). The chimeric polypeptide is preferably sufficiently soluble in phosphate buffered saline (PBS). Preferred levels of solubility in PBS for the chimeric lysins is at least about 1 mg/ml and more preferably at least about 3 mg/mL in PBS. While native staphylococcal bacteriophage lysins are typically insoluble in PBS, the chimeric lysins comprising an endopeptidase domain of a first lysin (e.g., Twort S. aureus lysin) bound to the CWT domain of SEQ ID NO:1 are surprisingly soluble in PBS (e.g., at least about 1 mg/ml, and typically about 3 mg/ml or greater). One example of such a lysin is provided in SEQ ID NO:2 (AD127), shown in FIG. 5A and consisting of the Twort lysin endopeptidase domain attached to the phiNM3 CWT domain (SEQ ID NO:1). The isolated polypeptide of SEQ ID NO:2 (AD 127) was constructed by engineering S. epidermidis autolysin amidase and Twort lysin endopeptidase domains upstream of phiNM3 CWT domain, respectively. Chimera AD 126 had no expression or activity but AD 127 was soluble and had very high activity but low expression. To overcome low expression of AD 127 construct, the entire chimera gene was cloned into expression vector pJML6 to generate pAD 138. The expression, solubility and activity of AD 127 from the pAD138 construct was very high. Therefore, this chimera was named 'ClyS' for Chimeric lysin for Staphylococcus (FIG. 5A).

ClyS (SEQ ID NO:2) contains 280 amino acid residues with a deduced molecular mass of 31956 Da and a theoretical isoelectric point of 9.17, and was purified by two-step column chromatography to >90% homogeneity. ClyS had a molecular mass of approximately 31 kDa by SDS/PAGE (FIG. 6) which was confirmed by gel filtrations chromatography, suggesting that the protein exists as a monomer and is not proteolytically processed (data not shown).

Figure 7:
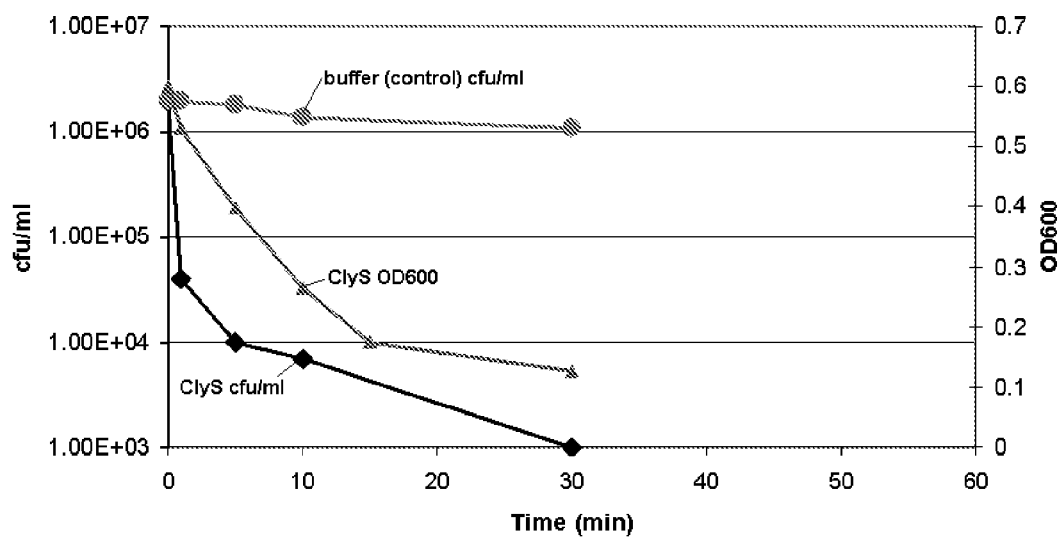
FIG. 7 is a graph showing the activity of ClyS against *S. aureus* in vitro. *S. aureus* strain 8325-4 cells were resuspended in 20 mM phosphate buffer (pH 7.4), incubated with 50 U of ClyS and OD600 (filled triangles) monitored by a spectrophotometer. Control experiments (filled squares) were performed under the same conditions with buffer alone. Viability (filled diamonds) of cells, shown as colony-forming units/ml, was determined by serially diluting and plating the cells.

The unit activity of ClyS was defined by measuring the spectrophotometric loss of turbidity, indicative of cell lysis, of S. aureus 8325-4 cells upon adding serial dilutions of ClyS. In our assays, 5 micrograms of ClyS corresponded to 1 U of lytic activity. When 50 U of ClyS was added to exponentially growing 8325-4 cells the OD600 dropped to baseline within 5 min (FIG. 7). To confirm that the observed cell lysis corresponds to cell death, staphylococcal viability was determined by enumerating aliquots from the lytic reaction at various time points. A decrease in viability of approximately 3-logs was observed in 30 min (FIG. 7).

Figure 8:
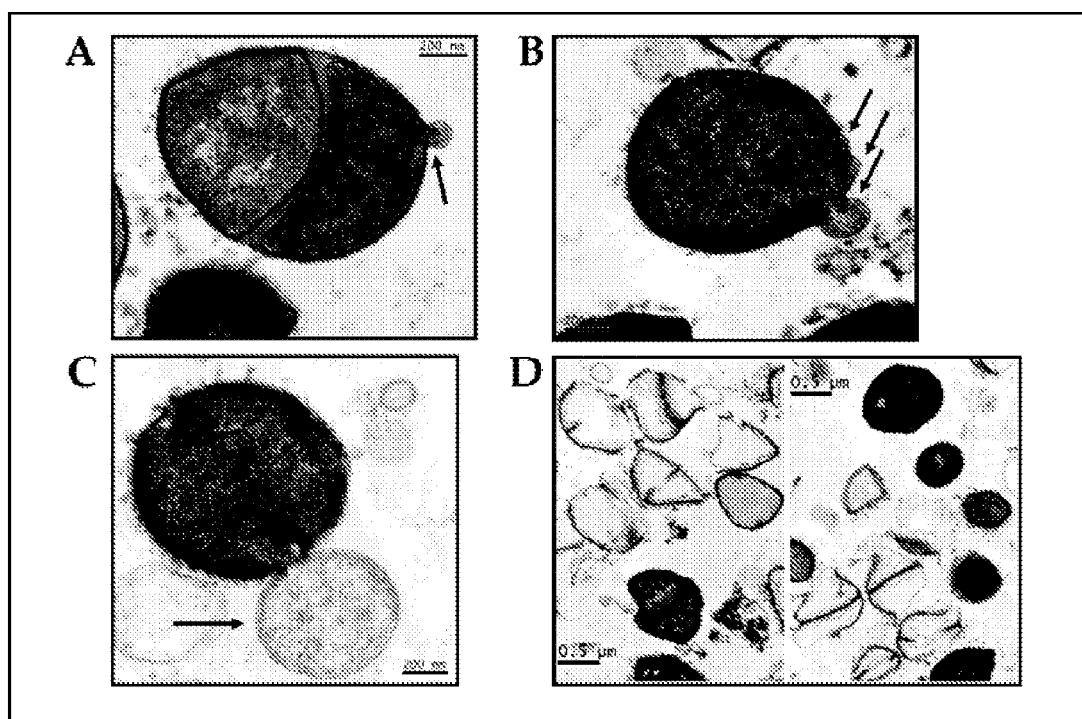
FIG. 8 is a series of micrographs showing that ClyS causes cell wall disruption and ultimately lysis of 8325-4 cells.

The lytic effect on S. aureus 8325-4 cells exposed to 50 U of ClyS for 1-3 min was visualized by transmission electron microscopy. Typical of lysin activity observed previously, localized degradation of the cell wall was observed at single (FIG. 8A) or multiple sites (FIG. 8B). However, unlike other lysins, the sites of degradation on the cell was not restricted to the septal or polar positions but was randomly distributed. This resulted in extrusions and rupture of the cell membrane (FIG. 8C) and subsequent loss of cytoplasmic contents and formation of cell-ghosts (FIG. 8D).

Figure 9A:
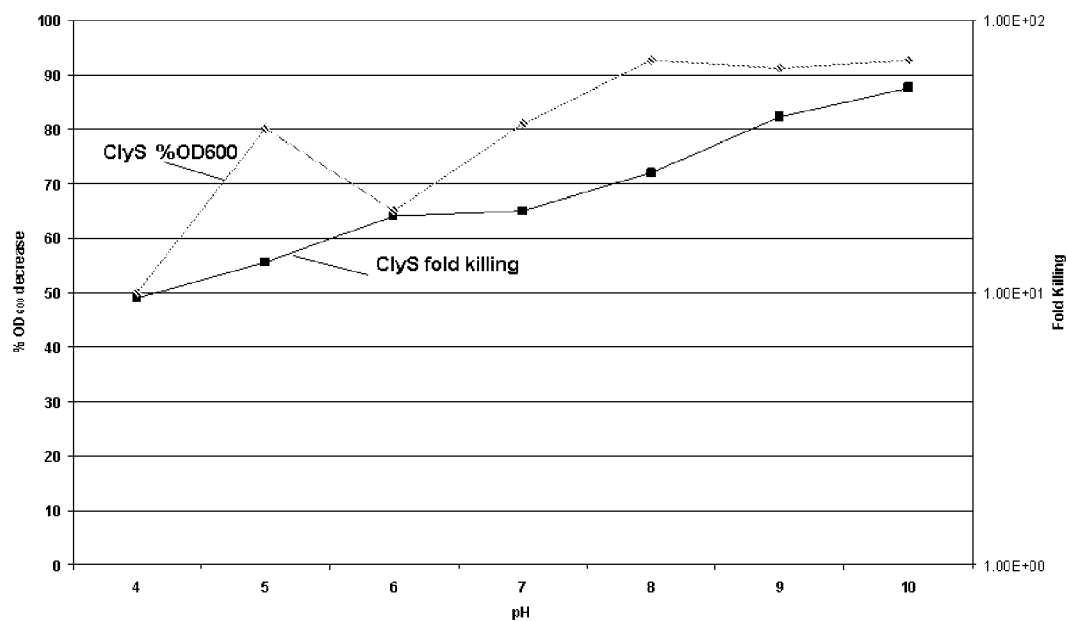
FIGS. 9A and 9B are graphs showing the activity of ClyS in various pH and salt concentration conditions.
Figure 9B:
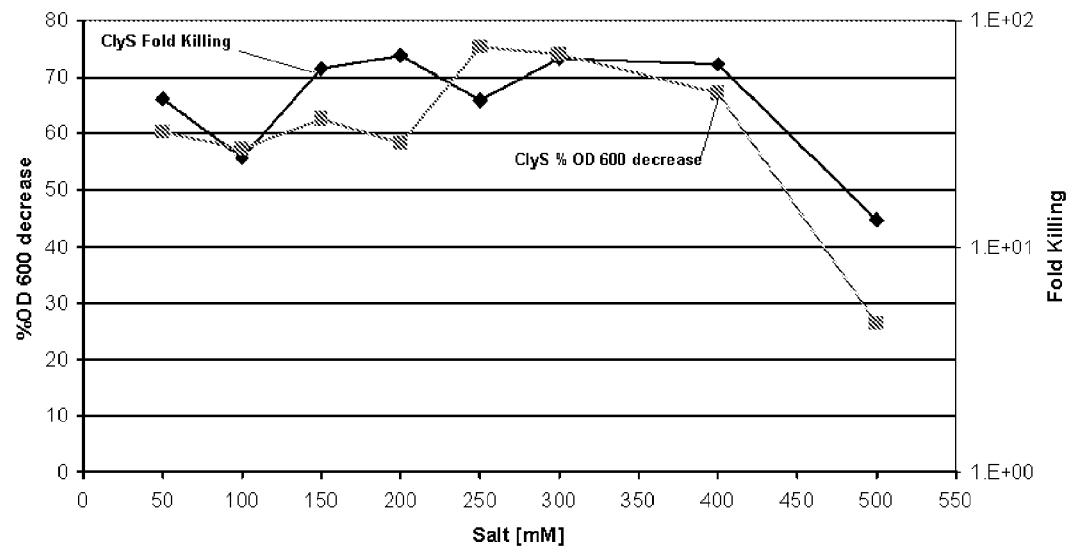

The effect of pH on the activity of ClyS was determined by measuring the drop in $OD_{600}$ or cell viability at different pH values. We observed that ClyS was active over a wide range of pH values but was most active between pH 9 and 10. However, ClyS retained partial yet significant activity at physiological pH (FIG. 9A). Similarly, the effect of salt concentration on activity of ClyS was also determined. ClyS displayed activity in a wide range of salt concentrations (FIG. 9B). While its activity deteriorated above 400 mM NaCl, at physiological concentrations ClyS functioned well.

Figure 10:
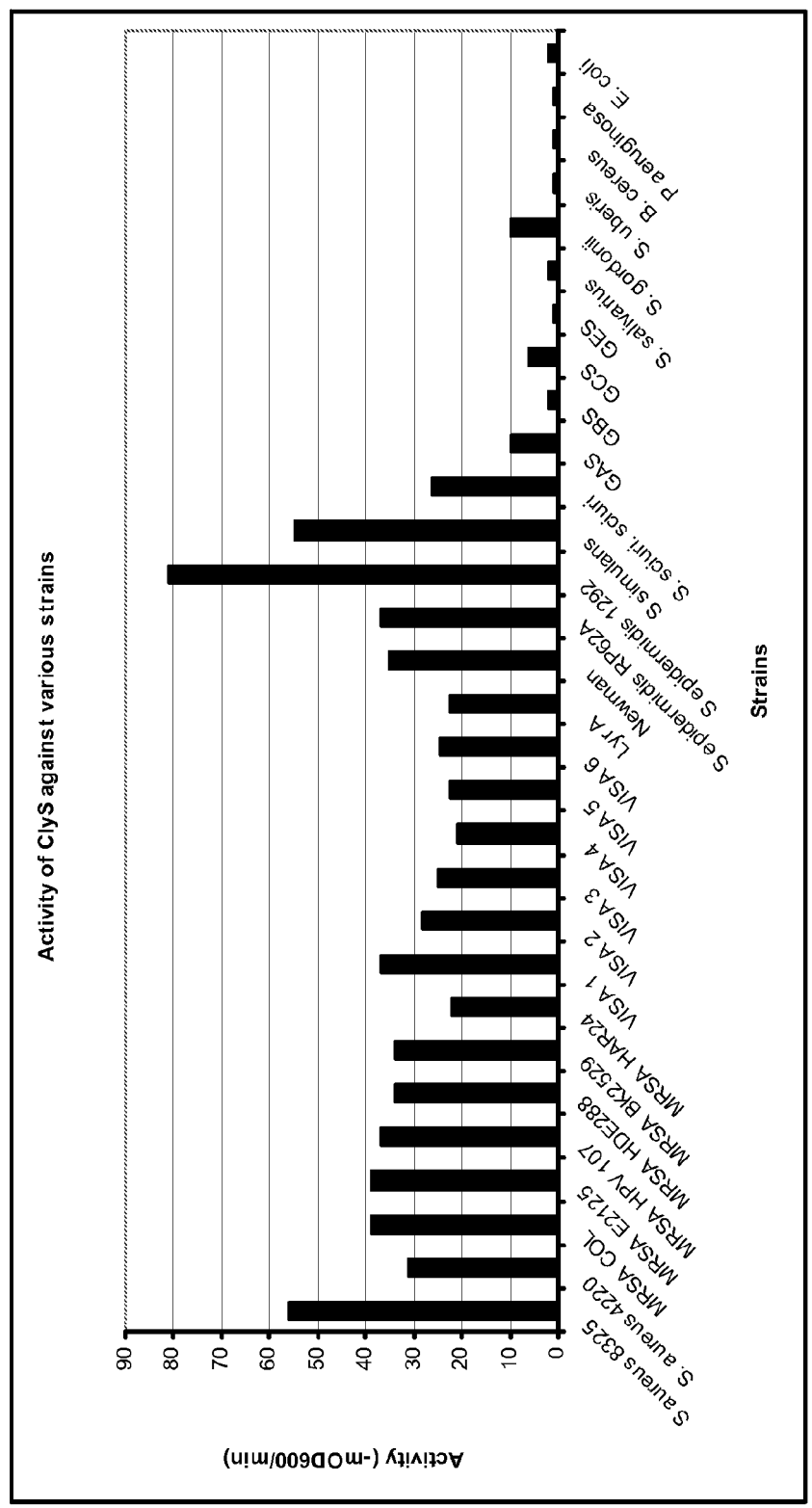
FIG. 10 is a bar graph showing that ClyS exerts specific killing of staphylococci. Log-phase cultures of different bacteria were exposed to 50 U of ClyS for 15 minutes. Fold killing was calculated as described in FIG. 8 legend.

Muralytic activity of ClyS was tested on a number of bacterial strains representing a variety of species which were divided into sets (Table 1 and FIG. 10). Set I consisted of S. aureus strains including methicillin-sensitive S. aureus (MSSA) and MRSA. ClyS was active against MSSA and MRSA although differences were observed between S. aureus strains. Set II consisted of different species of staphylococci including S. epidermidis, S. simulans and S. sciuri. ClyS was active not only against S. epidermidis including the biofilm-forming strain RP62A but was also active against S. simulans and S. sciuri suggesting that ClyS recognizes an epitope in the cell wall that is present in all staphylococcal cells. Set III consisted of a mix of Gram-positive and Gram-negative bacteria including representatives of group A, B, C and E streptococci, oral streptococcal species including S. gordonii, and S. salivarius, as well as S. uberis, Bacillus cereus, Pseudomonas aeruginosa and E. coli. ClyS exhibited no activity against any of these organisms.

In another embodiment, a chimeric peptide comprises an isolated polypeptide comprising an endopeptidase domain of the S. aureus Twort lysin upstream of the lyphostaphin CWT domain. One example of such a lysin is provided in SEQ ID NO:3 (AD119).

In another embodiment, lytic compositions may comprise a mixture of two or more lysins. The mixture may include a first polypeptide and a second peptide where one or both of the polypeptides may lack a desired level of lytic activity, but the mixture provides desirably specific and effective lytic activity against a bacteria of interest. For example, a composition may include an isolated first polypeptide comprising an endopeptidase domain of the S. aureus Twort lysin upstream of the lyphostaphin CWT domain combined with a second isolated polypeptide comprising an S. epidermidis autolysin amidase domain upstream of the lysostaphin CWT domain. One example of such a composition comprises a mixture of SEQ ID NO:3 (AD119) and SEQ ID NO:4 (AD112).

In some examples, the present disclosure pertains to lytic enzymes as a prophylactic treatment for preventing infection those who have possibly been exposed to S. aureus bacteria, or as a therapeutic treatment for those who have already become ill from the infection. The phage associated lytic enzymes described herein are specific for *S. aureus* bacteria and preferably effectively and efficiently break down the cell wall of the *S. aureus* bacteria.

The chimeric lytic enzyme polypeptides described herein may also be employed as a therapeutic agent. The lytic enzyme polypeptides of the present invention can be formulated according to known methods to prepare pharmaceutically useful compositions, whereby the lytic enzyme product hereof is combined in admixture with a pharmaceutically acceptable carrier vehicle. Compositions which may be used for the prophylactic and therapeutic treatment of a *S. aureus* bacteria infection also includes the shuffled and/or chimeric enzyme and a means of application (such as a carrier system or an oral delivery mode) to the mucosal lining of the oral and nasal cavity, such that the enzyme is put in the carrier system or oral delivery mode to reach the mucosa lining.

In one preferred embodiment, a *Staphylococcus* chimeric lysin, such as a lysin of SEQ ID NO:2 (ClyS), is administered as an antibacterial composition in combination with a suitable pharmaceutical carrier. In certain embodiments, the amount of the chimeric bacteriophase lysin present is a therapeutically effective amount. "Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™. These antimicrobial/pharmaceutical compositions may be administered locally or systemically.

Routes of administration include topical, ocular, nasal, pulmonary, buccal, parenteral (intravenous, subcutaneous, and intramuscular), oral, parenteral, vaginal and rectal. Also administration from implants is possible. The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated [see, for example, J Pharm Sci, 88 (10), 955-958 by Finnin and Morgan (October 1999).]

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques. The compounds of the invention may also be administered intranasally or orally by inhalation, typically in the form of a aerosol.

Suitable antimicrobial preparation forms are, for example granules, powders, tablets, coated tablets, (micro) capsules, suppositories, syrups, emulsions, microemulsions, defined as optically isotropic thermodynamically stable systems consisting of water, oil and surfactant, liquid crystalline phases, defined as systems characterized by long-range order but short-range disorder (examples include lamellar, hexagonal and cubic phases, either water- or oil continuous), or their dispersed counterparts, gels, ointments, dispersions, suspensions, creams, aerosols, droplets or injectable solution in ampule form and also preparations with protracted release of active compounds, in whose preparation excipients, diluents, adjuvants or carriers are customarily used as described above. The pharmaceutical composition may also be provided in bandages or in sutures or the like.

Many orthopedic surgeons consider that humans with prosthetic joints should be considered for antibiotic prophylaxis. Late deep infection by *S. aureus* is a serious complication sometimes leading to loss of the prosthetic joint and is accompanied by significant morbidity and mortality. It may therefore be possible to extend the use of the chimeric bacteriophage lysin described herein (e.g., SEQ ID NO:2) as a replacement for or for use in combination with prophylactic antibiotics in this situation. The chimeric bacteriophage lysin may be administered by injection with a suitable carrier directly to the site of the orthopedic device in situ to clear the infection, or on a surface of the device prior to implantantation. Other injection routes, such as subcutaneous, intramuscular, or intraperitoneal, can be used. Alternative means for administration include transmucosal and transdermal administration using penetrants such as bile salts or fusidic acids or other detergents. In addition, if a polypeptide or other compounds of the present invention can be formulated in an enteric or an encapsulated formulation, oral administration may also be possible. Administration of these compounds may also be topical and/or localized, in the form of salves, pastes, gels, and the like.

Prior to, or at the time the enzyme is put in the carrier system or oral delivery mode, it may be desirable for a chimeric peptide described herein to be administered or formulated in a stabilizing buffer environment, maintaining a pH range between about 5.0 and about 7.5. Prior to, or at the time the chimeric peptide is put in the carrier system or oral delivery mode, the enzyme may be in a stabilizing buffer environment for maintaining a suitable pH range, such as between about 5.0 and about 8.0, including a pH of about 5.0, 6.0, 7.0, 8.0 or any pH interval of 0.05 therebetween, or any interval that is a multiple of 0.05 therebetween, including pH values of 5.2, 6.5, 7.4, 7.5 and 8.5.

There are a number of advantages to using lytic enzymes to treat bacterial infections. The modular design of lysins, with their distinct catalytic and binding domains, makes them ideal for domain swapping experiments in which bacterial specificities and catalytic activities can be improved or adapted for use against alternate pathogens. Since the catalytic and binding targets of lysins (peptidoglycan and associated carbohydrates, respectively) are largely essential for viability, lysin resistance will be rare.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

The formulations to be used for in vivo administration are preferably sterile. This is readily accomplished by filtration through sterile filtration membranes, prior to or following lyophilization and reconstitution. Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems. When treating a bacterial exposure or infection, the lytic enzyme may be administered in any suitable fashion, including parenterally or through the oral or nasal cavity.

Dosages and desired drug concentrations of pharmaceutical compositions of the present invention may vary depending on the particular use envisioned. The determination of the appropriate dosage or route of administration is well within the skill of an ordinary physician. Animal-experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

When in vivo administration of a chimeic peptide lysin is employed, normal dosage amounts may vary from about 10 ng/kg to up to 1000 mg/kg of mammal body weight or more per day, or about 1 µg/kg/day to 10000 mg/kg/day, depending upon the route of administration. Guidance as to particular dosages and methods of delivery is also provided below, as well as in the literature. It is anticipated that different formulations will be effective for different treatment compounds and different disorders, that administration targeting one organ or tissue, for example, may necessitate delivery in a manner different from that to another organ or tissue.

The effective dosage rates or amounts of the chimeric peptide to be administered parenterally, and the duration of treatment will depend in part on the seriousness of the infection, the weight of the patient, the duration of exposure of the recipient to the infectious bacteria, the seriousness of the infection, and a variety of a number of other variables. The composition may be applied anywhere from once to several times a day, and may be applied for a short or long term period. The usage may last for days or weeks. Any dosage form employed should provide for a minimum number of units for a minimum amount of time. The concentration of the active units of a chimeric peptide believed to provide for an effective amount or dosage of enzyme may be in the range of about 10, 20, 30, 40, 50, 60, 70, 80, 90, or 100 units/ml up to about 10,000,000 units/ml of composition, in a range of about 1000 units/ml to about 10,000,000 units/ml, and from about 10,000 to 10,000,000 units/ml.

Additionally, a number of methods can be used to assist in transporting the enzyme across the cell membrane. The enzyme can be transported in a liposome, with the enzyme be "inserted" in the liposomes by known techniques. Similarly, the enzyme may be in a reverse micelle. The enzyme can also be pegylated, attaching the polyethylene glycol to the non-active part of the enzyme. Alternatively, hydrophobic molecules can be used to transport the enzyme across the cell membrane. Finally, the glycosylation of the enzyme can be used to target specific internalization receptors on the membrane of the cell.

Another preferred embodiment provides for a composition comprising a *Staphylococcus* chimeric lysin bacterial binding protein such as a lysin of SEQ ID NO:2 (ClyS), with other lytic enzymes which are useful for sanitizing or decontaminating porous surfaces e.g. textiles, carpeting. Furthermore, the composition of lytic enzymes may be used to decontaminate veterinarian surgical or examination areas, where such areas may be thought to harbor infectious organisms susceptible to the bacteriostatic or bacteriocidal activity.

In a further preferred embodiment, a *Staphylococcus* chimeric lysin such as a lysin of SEQ ID NO:2 (ClyS) may be combined with other bacteriostatic or bacteriocidal agents useful for decontamination of inanimate solid surfaces suspected of containing infectious bacteria, or for decontamination of porous surfaces.

EXAMPLES

Example 1: Identification of Specific Binding Peptides and Development of Chimeric Lysins We conducted conserved domain searches of *Staphylococcus*-specific phage and prophage lysin protein sequences in the National Center for Biotechnology Information database. The lysins were classified based on homology to known domains in the database. We identified several lysins including the *S. aureus* phage phiNM3 lysin (protein accession number YP_908849), *S. aureus* prophage phi13 amidase (accession number NP_803402), *S. aureus* prophage MW2 amidase (accession number NP_646703.1), etc. that shared 100% sequence identity with each other and had a conserved CHAP domain within their catalytic domain. However, the C-terminal domain of these lysins did not display homology to any known domains in the database (FIG. 1).

Since the attempts to express a native staphylococcal lysin were unsuccessful, we decided to develop chimeric lysins by taking advantage of the modular nature of lysins. Traditionally, *Bacillus*-specific lysins are expressed at high levels and are soluble in *E. coli*. Therefore, our first attempt was to engineer a 16-amino acid peptide (4) that is conserved in several *S. aureus*-specific lysins (Lu J Z, Fujiwara T, Komatsuzawa H, Sugai M, Sakon J. 2006. Cell wall-targeting domain of glycylglycine endopeptidase distinguishes among peptidoglycan cross-bridges. (Lue et al. (2006) J. Biol. Chem. 281(1):549-58) The catalytic domain of the *Bacillus*-specific lysin PlyB was used to generate chimera AD 103 (FIG. 4) (SEQ ID NO: 13). The chimeras were tested for expression, solubility and activity. Then the entire C-terminal CWT domain of PlyB (6) was replaced by the putative C-terminal domain of *S. aureus* phage Twort lysin (8) to obtain AD 105 (SEQ ID NO:14). This chimera was not active and so we engineered the lysostaphin CWT domain (10) downstream of PlyB-catalytic domain (2) to get AD 107 (SEQ ID NO:15). Although this chimera had expression, the solubility was poor and there was no activity. The next step was to engineer a *S. epidermidis* autolysin amidase domain (12) upstream of the lysostaphin CWT domain (10) which resulted in AD 112 (SEQ ID NO:4). AD 112 expressed very well and the protein was also very soluble but there was no lytic activity. However, we observed that the S. aureus cells clumped when exposed to AD 112. Since the lysostaphin catalytic domain (an amidase) (10) in AD 112 was of bacterial origin, we attempted to engineer a phage-derived catalytic domain upstream of the lysostaphin CWT. For this, the endopeptidase domain in Twort lysin (14) was used to construct chimera AD 119 (SEQ ID NO:3). We observed poor expression for AD 119 but the chimera was soluble. Although in our lytic assays AD 119 alone did not show significant activity, when combined with chimera AD 112 the activity was significantly enhanced. Since we identified phiNM3 CWT domain from our conserved domains searches and observed that phiNM3 CWT exhibited Staphylococcus-specific binding, we constructed chimeras AD 126 (SEQ ID NO:16) and AD 127 (SEQ ID NO:2) by engineering S. epidermidis autolysin amidase (12) and Twort lysin endopeptidase (14) domains upstream of phiNM3 CWT domain (2) (SEQ ID NO:1), respectively. Chimera AD 126 had no expression or activity but AD 127 was soluble and had very high activity but low expression (FIG. 4). To overcome low expression of AD 127 construct, the entire chimera gene was cloned into expression vector pJML6 to generate pAD 138. The expression, solubility and activity of AD 127 from the pAD138 construct was very high. Therefore, this chimera was named 'ClyS' for Chimeric lysin for Staphylococcus. The amino acid sequence for ClyS (i.e., SEQ ID NO:2) is provided in FIG. 5A.

Example 2: Construction of the ClyS Chimeric Lysin

Bacterial strains (Table 1) were stored at −80° C. routinely grown at 37° C. Staphylococcal strains used in this study were grown in Trypticase Soy Broth (TSB) media, streptococcal strains were grown in THY (Todd-Hewitt broth, 1% wt/vol yeast extract) media, B. cereus and P. aeruginosa were grown in BHI (Brain Heart Infusion) media while E. coli was cultivated in LB (Luria Bertani) media.

The chimeric lysin was constructed by amplifying and ligating individual domains from respective genes. For this, the Twort endopeptidase domain was PCR amplified from plasmid pCR2.1 plyTW which contains the entire lysin (plyTW) gene using primers TW-Endo-NcoI-F: 5'-CTAGC-CATGGAAACCCTGAAACAAGCAG-3' (SEQ ID NO:5) and TW-Endo-PstI-R: 5'-ACATGCTGCAGAACCATAT-TGTAATTAATATTAGTTCTATC-3'(SEQ ID NO:6). The cell wall targeting (CWT) domain was PCR amplified from S. aureus strain 8325 genomic DNA using primers NM3-CBD-PstI-F: 5'-ACATGCTGCAGGGTAAATCTGCAAGTAAAATAACAG-3' (SEQ ID NO:7) and NM3-CBD-Hind-R: 5'-CCCAAGCT-TAAAACACTTCTTTCACAATCAATCTC-3'(SEQ ID NO:8). The two PCR amplicons were ligated using the PstI restriction endonuclease site. The ligated product was cloned into pBAD24 vector using the NcoI-HindIII cloning sites to generate recombinant plasmid pAD127. In the second step, the entire DNA fragment corresponding to clyS was PCR amplified from pAD124 using primers NM3-Lys-Xba-F: 5'-CTAGTCTAGAGGTGGAATAATGAAAA-CATACAGTGAAGCAAG-3' (SEQ ID NO:9) and primer NM3-CBD-Hind-R(SEQ ID NO:8). The PCR product was cloned into expression vector pJML6 to generate pAD138. The sequence of ClyS was confirmed by sequencing. The recombinant plasmid pAD138 was transformed into E. coli DH5a cells.

Example 3: Overexpression and Purification of ClyS

ClyS was induced overnight from E. coli DH5a (pAD138) cells with lactose (10 g/500 ml final concentration) at 30° C. Cells were harvested by centrifugation, resuspended in buffer A (20 mM phosphate buffer (PB), 1 mM DTT (dithiothreitol)) and lysed by an EmulsiFlex-05 high pressure homogenizer (Avestin) at 4°° C. The lysates were cleared by centrifugation (2×50,000×g) for 30 minutes at 4° C. and the supernatant applied to a CM-sepharose column (Amersham Pharmacia, Piscataway, N.J.). ClyS was eluted with buffer A+1M NaCl using a linear gradient of 0-50% B in 15 columns volumes. Fractions were analyzed for lytic activity as previously described (Daniel et al, 2001). Fractions displaying lytic activity were pooled and dialyzed overnight against buffer B (PB, 1 mM DTT, 50 mM NaCl). The dialyzed sample was applied to a hydroxylapatite (Macro-Prep TypeII 40 μm, BioRad) column and eluted with elution buffer (500 mM PB+50 mM NaCl+1 mM DTT) using a linear gradient of 0-100% B in 20 columns volumes. The fractions were analyzed by SDS-PAGE and for lytic activity. Active clean fractions of ClyS were pooled and dialyzed against buffer B. Protein concentration was determined with the BCA method (Sigma, St. Louis, Mo.).

Example 4: Quantification of ClyS Activity

ClyS activity was measured as previously described (Daniel et al, 2001), with some modifications. Briefly, S. aureus strain 8325-4 was grown to an $OD_{600}$ of 0.25-0.3, centrifuged, and resuspended in PB to a final $OD_{600}$ of 0.8-1.0. Two-fold serial dilutions of purified ClyS (100 μl) were added to 100 μl of bacterial suspension in 96-well plates (Costar) and the decrease in OD600 was monitored by a Spectramax Plus 384 spectrophotometer (Molecular Devices) over 30 min at 37° C. ClyS activity in units per milliliter was defined as the reciprocal of the highest dilution of lysin that decreased the absorbance by 50% in 15 minutes.

Example 5: Measuring In Vitro ClyS Activity

The viability assay of ClyS was tested as previously described (Nelson et al, 2001). Briefly, logphase cultures of S. aureus strain 8325-4 were resuspended in PB to $OD_{600}$ of 0.8-1.0. 50 U of ClyS or the corresponding volume of PB was added to bacterial cells and aliquots were removed, serially diluted, and plated at 1, 5, 10, 30, and 60 minutes to assess the viability of the treated and control cells. All experiments were performed in triplicate. The activity of ClyS on various bacterial strains was tested as described previously (Schuch et al, 2002). Briefly, logphase bacterial cells were treated with 50 U of ClyS at 37° C. for 15 minutes. The samples were serially diluted and plated. Control experiments with the addition of phosphate buffer (pH 7.0) were performed under the same conditions.

Example 6: Measuring ClyS Activity as a Function of pH and Salt Profile

The effect of pH on ClyS activity was determined as previously described using the universal buffer system pH 4-10 (Yoong et al). Briefly, logphase 8325-4 cells were resuspended in the universal buffer system and incubated with 50 U of ClyS for 15 minutes. The final pH of each reaction was checked by pH paper. The samples were serially diluted and plated. In controls, PB replaced ClyS.

Similarly the effect of salt concentration on the lytic activity of ClyS was determined by incubating 50 U of ClyS with logphase 8325-4 cells in PB containing NaCl at a final concentration of 25-500 mM for 15 minutes. The samples were serially diluted and plated to determine the viability counts.

Example 7: Microscopy of ClyS

*S. aureus* strain 8325-4 was grown to log-phase, centrifuged and resuspended in PBS to an absorbance at 600 nm of 1.0. The bacterial suspension was incubated with 50 U of ClyS at room temperature. The lytic reaction was terminated after 1 minute and 5 minutes by adding glutaraldehyde (final concentration 2.5%). The suspension was pelleted by centrifugation and overlaid with 2.5% glutaraldehyde in 0.1 M cacodylate buffer (pH 7.4). The samples were then postfixed in 1% osmium tetroxide, block stained with uranyl acetate and processed according to standard procedures by The Rockefeller University Electron Microscopy Service.

Flourescent labeling and binding analyses were performed on phiNM3 CWT. *S. aureus* strain 8325-4 genomic DNA was used to amplify the putative CWT of phiNM3 lysin using primers NM3-FWD 5'-CATGC-CATGGGTAAATCTGCAAGTAAAATAACAG-3' (SEQ ID NO:10) and NM3-REV 5'-CCCAAGCT-TAAAACACTTCTTTCACAATCAATCTC-3'(SEQ ID NO:11). The resulting amplicon was cloned into the arabinose-inducible expression vector pBAD24. Positive clones containing the insert were confirmed by sequencing. The approximately 10-kDa phiNM3 CWT protein was expressed and the protein was purified in one step by cation-exhange chromatography. The purified protein (1 mg/ml) was incubated with 10 µl of FITC (1 mg/ml) for 1 hour. Excess FITC was removed on a desalting column. The labeled-protein (50 µg) was incubated with bacterial cells for 10 minutes, washed 3× with phosphate-buffered saline (pH 7.4) and observed under fluorescence microscope.

Example 8: Measuring In Vivo Activity of ClyS

MRSA strain would be grown to log-phase, centrifuged and resuspended to a predefined titer of about 1010 cfu/ml. For intranasal infection, 6-wk-old female C57BL/6J, outbread Swiss or BALB/c mice (weight range 22 to 24 g, Charles River Laboratories, Wilmington, Mass.) would be anesthetized with a mixture of ketamine (Fort Dodge Animal Health, Fort Dodge, Iowa, 1.2 mg/animal) and xylazine (Miles Inc., Shawnee Mission, Kans., 0.25 mg/animal), and inoculated with 15 µl of the bacterial suspension per nostril (n=10). The animals would be divided into 2 groups and administered various concentrations of ClyS or sterile saline intraperitoneally six hours after infection and every six hours thereafter for 3 days. The survival rate for each group would be observed up to 7 days post infection. For intraperitoneal infection, mice would be infected intraperitoneally with 100 µl of the bacterial suspension (n=10). The animals would be divided into 2 groups and administered various concentrations of ClyS or sterile saline intraperitoneally six hours after infection and every six hours thereafter for 3 days. The survival rate for each group would be observed up to 7 days post infection.

Example 9. The Linker Region by Itself does not Confer Solubility to a Chimera

Since the ClyS construct was the only chimera that was highly soluble and active against staphylococci, we hypothesized that the linker region comprising of amino acid residues 142 through 185 of ClyS may be crucial for solubility. We had previously cloned and expressed the native phiNM3 lysin and observed that the protein was insoluble. To test this hypothesis, we replaced the endopeptidase domain of ClyS with the amidase domain of phiNM3 lysin upstream of the linker region of ClyS (ami-link-ClyS) and expressed the chimera (data not shown). We observed that similar to the native phiNM3 lysin, the ami-link-ClyS chimera was insoluble and expressed as inclusion bodies. We also tested the lysates of ami-link-ClyS for activity against staphylococci and did not observe any lytic activity confirming that the protein was insoluble and therefore inactive. Thus, it is the unique combination of the N and C terminal domains that are the subject of this patent that allow for a soluble complex to occur and behave as described herein.

Example 10. In Vivo Nasal Decolonization of MRSA by ClyS

Figure 11:
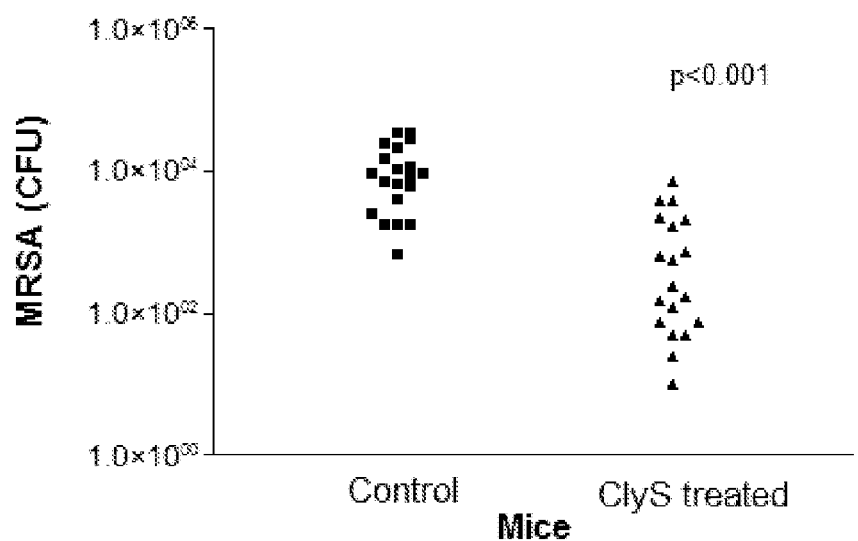
FIG. 11 depicts a graph of the CFU of MRSA from individual MRSA infected mice after being administered phosphate buffered saline pH 7.3 (control) or ClyS (630 µg).

Carriage of both MSSA and MRSA in the human anterior nares is the major reservoir for *S. aureus* infection. Studies have shown that roughly 80% of the population could be nasally colonized by *S. aureus*, and that colonization can be an increased risk factor for developing other more serious *S. aureus* infections (Kluytmans, J., A. van Belkum. 1997. Nasal carriage of *Staphylococcus aureus*: epidemiology, underlying mechanisms, and associated risks. Clin Microbiol Rev 10(3): 505-20.). Elimination of nasal carriage in the community or in the hospital setting thus could possibly reduce the risk of infection and slow the spread of drug resistant *S. aureus* (Kluytmans et al. (1997)). To study the potential of ClyS to reduce MRSA colonization of the nasal mucosa, C57BL/6J mice were intranasally inoculated with ~2×10$^7$ of a spontaneously streptomycin resistant strain of MRSA (191-SM$^R$). Twenty-four hours post-infection mice were administered three doses hourly of either phosphate buffered saline (control) or ClyS (960 µg) into the nasal passages. One hour after the last treatment, mice were sacrificed and bacteria colonies were enumerated on Spectra MRSA agar, (a selective chromogenic medium developed to diagnostically detect MRSA nasal colonization) and Columbia blood agar. No significant differences in CFU were obtained between plating to Spectra MRSA agar or Columbia blood agar (Data not shown) Three independent experiments were performed to evaluate a total 20 mice for each treatment group (FIG. 11). Compared to the buffer alone control (Avg. 12,273 CFU/cavity), ClyS treatment (Avg. 1198 CFU/cavity) significantly (p<0.001) reduced the mean CFU on the nasal mucosa.

Example 11. ClyS Treatment of Systemic MRSA Infections

Figure 12:
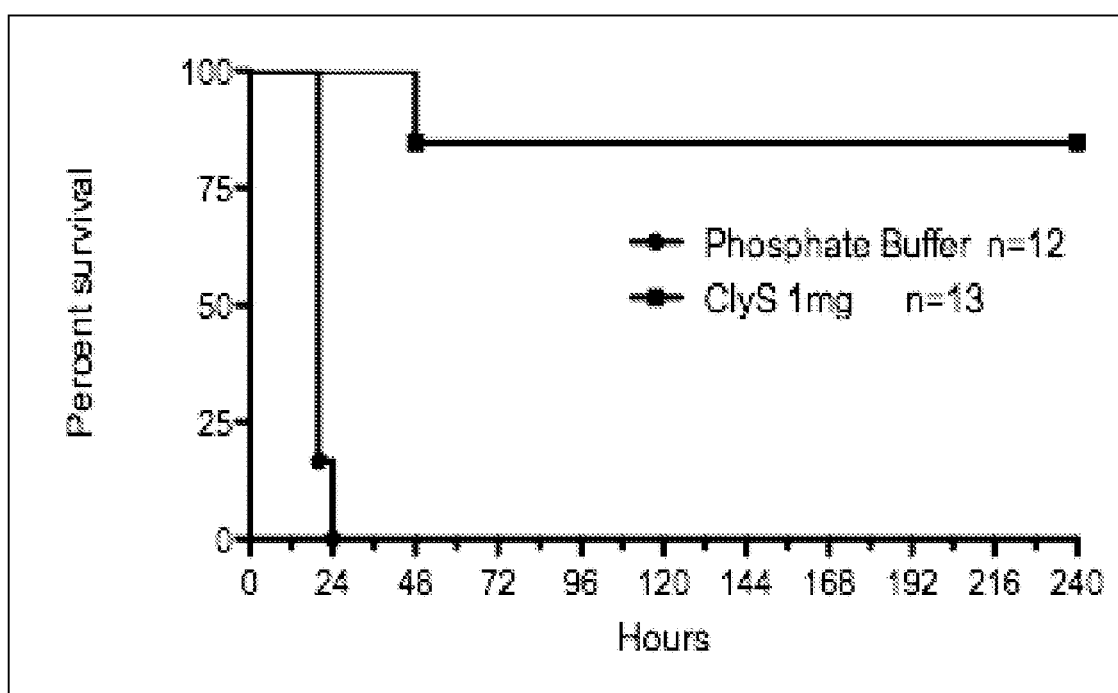
FIG. 12 depicts Kaplan Meier Survival Curves showing the effect of ClyS on preventing death in mice injected with MRSA compared with phosphate buffer control.

In order to assess whether ClyS treatment could prevent death resulting from systemic MRSA infections, 4 week old FVB/NJ mice were intraperitonally injected with 5×10$^5$ CFU of the community-acquired MRSA strain MW2 in 5% mucin. Preliminary experiments determined that 5×10$^5$ CFU was 10× the LD$_{100}$ dose for a twenty-four hour period. Furthermore, within 3 hours of IP injection the MRSA infection was systemic, i.e., MRSA were recovered in high numbers from heart, liver, spleen, and kidney (data not shown). Treatment occurred three hours post-infection, with either 20 mM phosphate buffer or 1 mg of ClyS in 20 mM phosphate buffer injected IP (intraperitoneally). Mice were then monitored for survival over ten days. The results from three independent experiments were combined (ClyS treatment, n=16; buffer treatment, n=14) and the mice survival data plotted with a Kaplan Meier Survival curve (FIG. 12). Within twenty-four hours all of the control mice died of bacterial sepsis, while only 2/16 of ClyS treated mice died at forty-eight hours, and the remaining mice (14/16, 88%) survived over the course of the experiments (FIG. 12).

Example 12. ClyS Showed Synergistic Interaction with Vancomycin and Oxacillin

Figure 13:
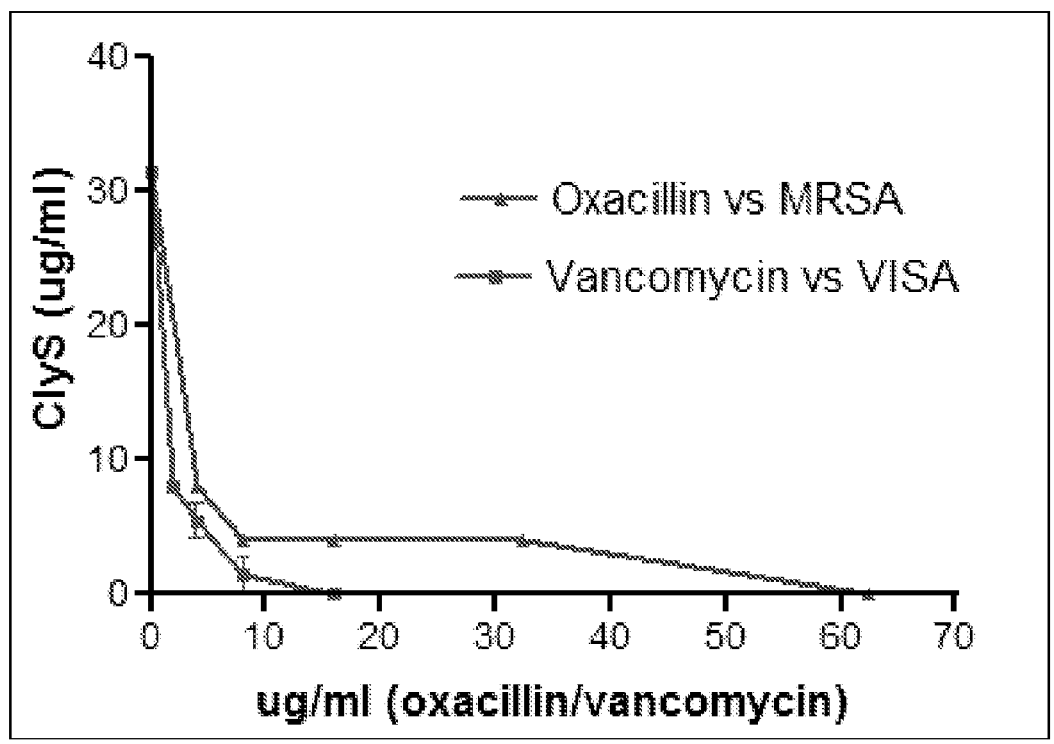
FIG. 13 depicts an isobologram for a checkerboard broth microdilution study of the effect of vancomycin on VISA (vancomycin-resistant *Staphylococcus aureus*) or oxacillin on MRSA with increasing amounts of ClyS.

We used the checkerboard broth-microdilution assay to test the interaction of ClyS with vancomycin and with oxacillin. The vancomycin MIC for VISA strain Mu50 was 8 µg/ml and the oxacillin MIC for MRSA strain COL was 32 µg/ml, while the ClyS MIC was 6 and 8 U/ml for both strains tested (Mu50 and COL respectively). Isobolograms for ClyS with vancomycin and ClyS with oxacillin was plotted by transcribing the enzyme concentrations along the inhibitory line on the microtiter plate in an x/y plot. The shape of the curves for both interactions were characteristic of a synergistic interaction (FIG. 13) and were further confirmed by calculating the ΣFICI for both interactions which was ≤0.5.

Figure 14:
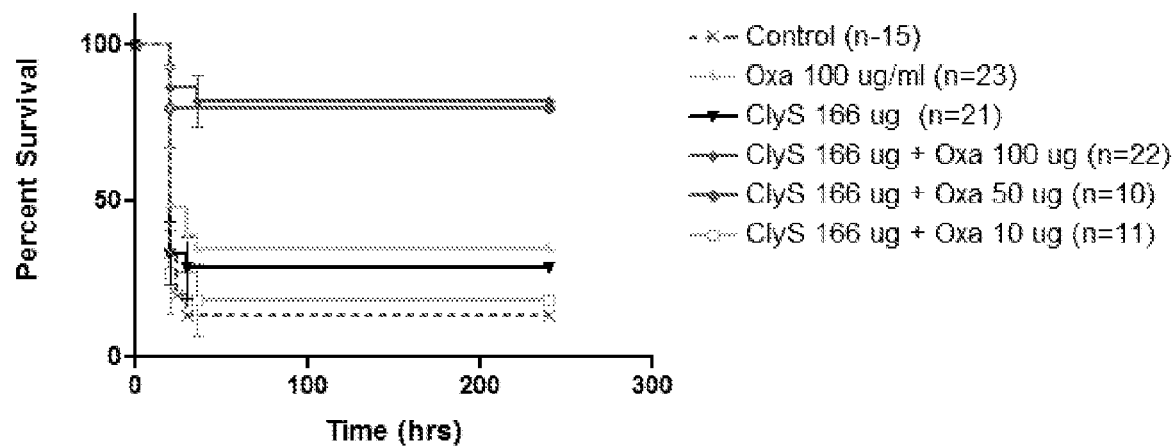
FIG. 14 depicts Kaplan Meier Survival Curves showing the effect of oxacillin alone or in combination with ClyS.

Example 13. In Vivo Synergy of Oxacillin and ClyS in the Treatment of Systemic MRSA Infections In vitro experiments showed that ClyS acted synergistically with oxacillin (FIG. 14). To determine if this effect could be seen in our systemic MRSA infection model, FVB/NJ mice were intraperitonally injected with ~5×10$^5$ CFUs of the MRSA strain MW2 as above. Three hours post infection mice were treated in parallel, with a lower IP dose of 130 µg/mouse of ClyS combined with different concentrations of oxacillin (10-100 µg/mouse) or buffer alone controls. Preliminary experiments determined that an $ED_{30}$ dose of ClyS (130 µg/mouse) had minimal efficacy to evaluate the effect of combinatorial treatment with oxacillin (data not shown). Mice were monitored for survival for 10 days and the results of 5 independent experiments were combined and plotted in a Kaplan Meier Survival curve (FIG. 14). While only 30% (6/20 alive) to 35% (8/23 alive) of mice survived with individual treatments of either 130 µg/mouse of ClyS or 100 µg/mouse of oxacillin, respectively, neither differed significantly from the survival rate of the buffer alone control, 13% (2/15 alive). Conversely, a single dose of the combined treatment of intraperitoneal injected ClyS (130 µg) with either 0 µg or 50 µg of intramuscular injected oxacillin significantly increased mouse survival (80%, 8/10 alive; 82%, 18/22 alive respectively) compared to the individual treatments and buffer alone (FIG. 14).

Example 16

Figure 15:
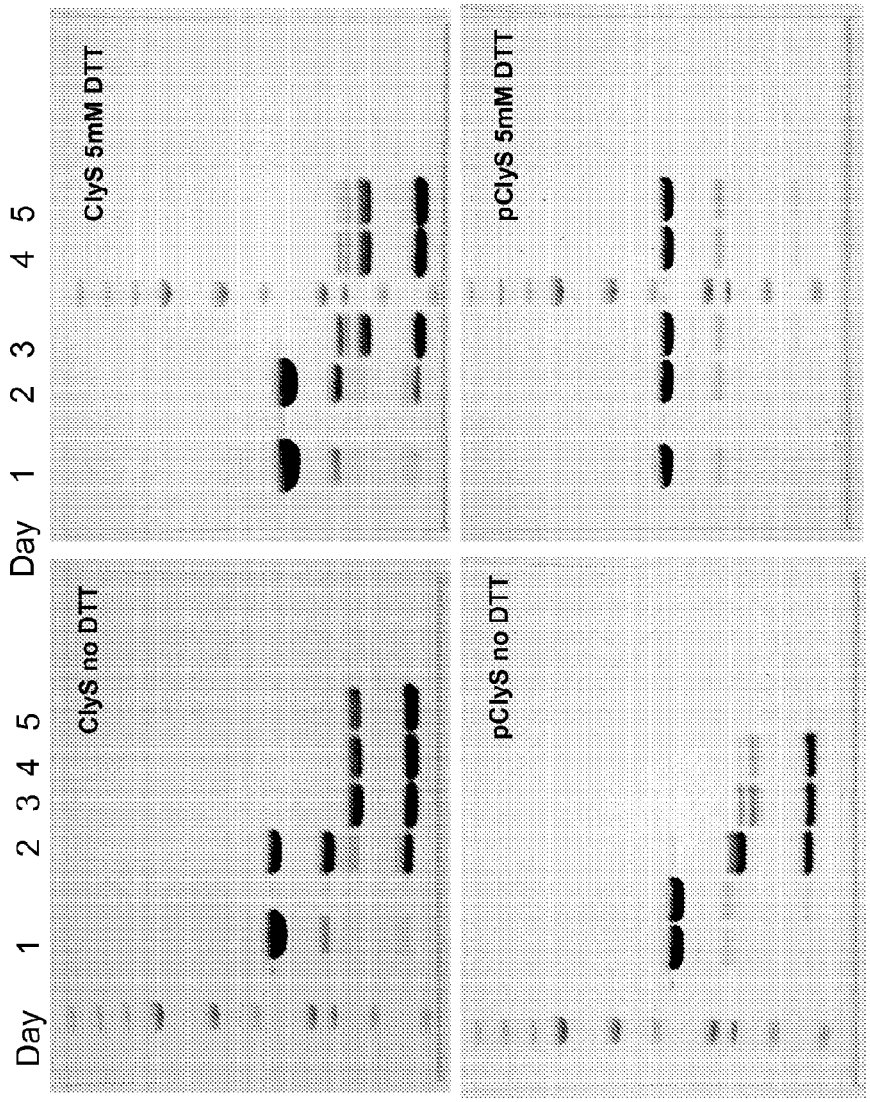
FIG. 15 depicts a photograph of a Coomassie-blue stained SDS-PAGE gel of a 5-day time-course at 21° C. of ClyS in the absence (top left gel) or presence of 5 mM DTT (top right gel), and pClyS in the absence (bottom left gel) or presence of 5 mM DTT (bottom right gel). About 20 micrograms of protein was loaded into each lane of the gel. The bottom right gel shows a much higher amount of intact pClyS in the presence of 5 mM DTT after 5 days compared to intact ClyS in the presence of 5 mM DTT after 5 days.

Modification of ClyS. The $G^{166}$ residue of ClyS (SEQ ID NO:2) was changed to a proline by site directed mutagenesis (creating pClyS). When the purified pClyS molecule (SEQ ID NO: 17) was subjected to stability studies at 21° C. for 5 days, the pClyS was found to be significantly more stable in the presence of 5 mM DTT the native ClyS with or without DTT (FIG. 15).

While the invention has been described and illustrated herein by reference to various specific materials, procedures, and examples, it is understood that the invention is not restricted to the particular materials, combinations of materials, and procedures selected for that purpose. Numerous variations of such details can be implied and will be appreciated by those skilled in the art.

We claim:

1. A combination of a chimeric lysin protein having a binding molecule cell wall targeting (CWT) domain SEQ ID NO:1, wherein SEQ ID NO:1 is removed from native N-terminal catalytic domain, or a variant of SEQ ID NO:1 removed from native N-terminal catalytic domain having at least 90% amino acid sequence identity to SEQ ID NO:1 and capable of binding specifically to staphylococci, attached or conjugated to an N-terminal cysteine- and histidine-dependent amidohydrolase/peptidase (CHAP) catalytic domain of another *Staphylococcus* lysin that does not natively have the same CWT as SEQ ID NO:1, wherein the chimeric protein has killing activity against *Staphylococcus aureus* and is capable of binding specifically to staphylococci, in combination with a bacteriostatic or bacteriocidal agent.

2. The chimeric protein in the combination of claim 1, wherein the variant of SEQ ID NO:1 has at least 95% amino acid sequence identity to SEQ ID NO: 1 and the chimeric protein has killing activity against *Staphylococcus aureus* and is capable of binding specifically to staphylococci.

3. The chimeric protein in the combination of claim 1, wherein the binding CWT domain corresponds to SEQ ID NO: 1 and the chimeric protein has killing activity against *Staphylococcus aureus* and is capable of binding specifically to staphylococci.

4. The chimeric protein in the combination of claim 1, wherein the catalytic domain is the Twort endopeptidase domain and comprises amino acids 1-186 of SEQ ID NO:2 and the chimeric protein has killing activity against *Staphylococcus aureus* and is capable of binding specifically to staphylococci.

5. The chimeric protein in the combination of claim 1, wherein the binding CWT domain corresponds to SEQ ID NO:1 and the catalytic domain is the Twort endopeptidase domain and comprises amino acids 1-186 of SEQ ID NO:2, wherein the chimeric protein comprises the polypeptide sequence of SEQ ID NO:2 or a variant thereof having at least 90% amino acid sequence identity to SEQ ID NO:2, and wherein the chimeric protein or variant has killing activity against *Staphylococcus aureus* and is capable of binding specifically to staphylococci.

6. The chimeric protein in the combination of claim 5, wherein the variant has at least 95% amino acid sequence identity to SEQ ID NO:2 and is capable of binding specifically to staphylococci and has killing activity against *Staphylococcus aureus*.

7. The chimeric protein in the combination of claim 1, wherein the chimeric protein has the polypeptide sequence of SEQ ID NO:2.

8. The combination of claim 1, wherein the bacteriostatic or bacteriocidal agent is an antibiotic.

9. The combination of claim 8, wherein the antibiotic is selected from vancomycin and oxacillin.

10. The combination of claim 1, wherein the bacteriostatic or bacteriocidal agent is another lytic enzyme.

11. The combination of claim 1, wherein the chimeric protein has killing activity against antibiotic-resistant staphylococci.

12. The combination of claim 1, wherein the combination has killing activity against antibiotic-resistant staphylococci.

13. The combination of claim 1, wherein the chimeric protein has killing activity against biofilm-forming staphylococci.

14. An anti-microbial composition for sanitizing or decontaminating porous or non-porous surfaces comprising the combination of claim 1.

15. A method for decontaminating inanimate surfaces suspected of containing infectious staphylococci bacteria comprising treatment of said surfaces with a bacteriocidal or bacteriostatically effective amount of the composition of claim 14.

16. A pharmaceutical composition comprising the combination of claim 1 and a pharmaceutically acceptable carrier.

17. The pharmaceutical composition of claim 16 which is formulated for topical, ocular, nasal, pulmonary, buccal, parenteral, oral, vaginal or rectal administration.

18. A method of treating a mammal with a staphylococcal infection comprising administering to said mammal the combination of claim 1.

19. A method of treating a mammal with a staphylococcal infection comprising administering to said mammal the combination of claim 4.

20. A method of treating a mammal with a staphylococcal infection comprising administering to said mammal the combination of claim 5.

21. A method of treating a mammal with a staphylococcal infection comprising administering to said mammal the pharmaceutical composition of claim 16.

22. A method of decolonizing staphylococci in a mammal colonized by staphylococci comprising administering to said mammal the combination of claim 1.

23. A method of decolonizing staphylococci in a mammal colonized by staphylococci comprising administering to said mammal the combination of claim 4.

24. A method of decolonizing staphylococci in a mammal colonized by staphylococci comprising administering to said mammal the combination of claim 5.

25. A method of decolonizing staphylococci in a mammal colonized by staphylococci comprising administering to said mammal the pharmaceutical composition of claim 16.

\* \* \* \* \*